(12) United States Patent
Ravel et al.

(10) Patent No.: US 11,389,491 B2
(45) Date of Patent: *Jul. 19, 2022

(54) MICROBIOME-BASED INFORMED METHOD TO FORMULATE LIVE BIOTHERAPEUTICS

(71) Applicant: University of Maryland, Baltimore, Baltimore, MD (US)

(72) Inventors: Jacques Ravel, Laurel, MD (US); Michael France, Baltimore, MD (US); Lindsay Rutt, Baltimore, MD (US); Bing Ma, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/223,710

(22) Filed: Apr. 6, 2021

(65) Prior Publication Data

US 2021/0220413 A1 Jul. 22, 2021

Related U.S. Application Data

(60) Division of application No. 16/917,661, filed on Jun. 30, 2020, now Pat. No. 10,967,012, and a continuation-in-part of application No. 16/800,702, filed on Feb. 25, 2020, now Pat. No. 11,037,655.

(60) Provisional application No. 62/972,243, filed on Feb. 10, 2020, provisional application No. 62/915,852, filed on Oct. 16, 2019.

(51) Int. Cl.
| | |
|---|---|
| A61K 35/742 | (2015.01) |
| A01N 63/00 | (2020.01) |
| A61K 39/00 | (2006.01) |
| A61K 39/38 | (2006.01) |
| A61K 35/74 | (2015.01) |

(52) U.S. Cl.
CPC ............ *A61K 35/742* (2013.01); *A61K 35/74* (2013.01)

(58) Field of Classification Search
CPC .................................................. A61K 35/742
See application file for complete search history.

(56) References Cited

U.S. PATENT DOCUMENTS

| | | |
|---|---|---|
| 8,846,027 B2 | 9/2014 | Kiss et al. |
| 10,169,541 B2 | 1/2019 | Apte et al. |
| 10,246,753 B2 | 4/2019 | Apte et al. |
| 10,967,012 B2* | 4/2021 | Ravel ................ A61K 35/742 |
| 11,037,655 B2* | 6/2021 | Ravel ................ G16B 30/20 |
| 2018/0114592 A1 | 4/2018 | Apte et al. |
| 2021/0244776 A1 | 8/2021 | Ravel et al. |

FOREIGN PATENT DOCUMENTS

| | | |
|---|---|---|
| WO | WO 2010/079991 | 7/2010 |
| WO | WO 2015/173693 | 11/2015 |
| WO | WO 2016/121865 | 8/2016 |
| WO | WO 2019/018348 | 1/2019 |

OTHER PUBLICATIONS

"Lactobacillus crispatus ST1 complete genome, strain ST1," NCBI GenBank Entry No. FN692037, Feb. 27, 2015, retrieved from https://www.ncbi.nlm.nih.gov/nuccore/FN692037.1/, 545 pages.
Agarwala et al., "Database Resources of the National Center for Biotechnology Information," Nucleic Acids Research, vol. 45 Database issue, Nov. 28, 2016, pp. D12-D17.
Attwood et al., "The PRINTS protein fingerprint database in its fifth year," Nucleic Acids Research, vol. 26, No. 1, Jan. 1, 1998, pp. 304-308.
Bohbot et al., "Efficacy and safety of vaginally administered lyophilized Lactobacillus crispatus IP 174178 in the prevention of bacterial vaginosis recurrence," Journal of Gynecology Obstetrics and Human Reproduction, vol. 47, No. 2, Nov. 28, 2017, pp. 81-86.
Bolger et al., "Trimmomatic: a flexible trimmer for Illumina sequence data," Bioinformatics, vol. 30, No. 15, Apr. 1, 2014, pp. 2114-2120.
Bru et al., "The ProDom database of protein domain families: more emphasis on 3D ," Nucleic Acids Research, vol. 33 Database issue, Jan. 1, 2005, pp. D212-D215.
Church et al., "Modernizing Reference Genome Assemblies," PLoS Biology, vol. 9, No. 7, Jul. 2011, 5 pages.
Crabtree et al., "Sybil: Methods and Software for Multiple Genome Comparison and Visualization," Methods in Molecular Biology: Gene Function Analysis, 2007, vol. 408, No. 6, pp. 93-108.
Dixon, "Vegan, a package of R functions for community ecology," Journal of Vegetation Science, vol. 14, Oct. 9, 2003, pp. 927-930.
Edwards et al., "The Cervicovaginal Microbiota-Host Interaction Modulates Chlamydia trachomatis Infection," mBio, vol. 10, No. 4, Jul. 2019, 18 pages.
Finn et al., "The Pfam protein families database: towards a more sustainable future ," Nucleic Acids Research, vol. 44, No. D1, Dec. 15, 2015, pp. D279-D285.
Haft et al., "The TIGRFAMs database of protein families," Nucleic Acids Research, vol. 31, No. 1, Jan. 1, 2003, pp. 371-373.
Huerta-Cepas et al., "eggNOG 4.5: a hierarchical orthology framework with improved functional annotations for eukaryotic, prokaryotic and viral sequences," Nucleic Acids Research, vol. 44, No. D1, Nov. 17, 2015, pp. D286-D293.

(Continued)

*Primary Examiner* — Gary B Nickol
*Assistant Examiner* — Lakia J Jackson-Tongue
(74) *Attorney, Agent, or Firm* — Sheridan Ross P.C.

(57) ABSTRACT

Methods of formulating live biotherapeutics are disclosed in which a deficiency or excess of a specific bacterial strain in a person's microbiome is identified by comparing a gene-specific characterization of the person's microbiome against a comprehensive, non-redundant reference gene catalog, and the biotherapeutic is formulated by selecting bacteria to address the deficiency or excess. Embodiments include the formulation of live biotherapeutics for improving the health of a person's vaginal microbiome, i.e. using a vaginal reference gene catalog, and may be suitable for ameliorating, treating, or preventing a malignancy such as a cancer of the female genitourinary system.

20 Claims, 5 Drawing Sheets

Specification includes a Sequence Listing.

(56) References Cited

OTHER PUBLICATIONS

Hunter et al., "InterPro: the integrative protein signature database," Nucleic Acids Research, vol. 37 Database issue, Oct. 21, 2008, pp. D211-D215.
Ito et al., "Transposon Mutagenesis of Probiotic Lactobacillus casei Identifies asnH, an Asparagine Synthetase Gene Involved in Its Immune-Activating Capacity," PLoS One, vol. 9, No. 1, Jan. 2014, 10 pages.
Kanehisa et al., "KEGG for integration and interpretation of large-scale molecular data sets," Nucleic Acids Research, vol. 40, No. D1, Nov. 10, 2011, pp. D109-D114.
Kristensen et al., "Orthologous Gene Clusters and Taxon Signature Genes for Viruses of Prokaryotes," Journal of Bacteriology, vol. 195, No. 5, Mar. 2013, pp. 941-950.
Kwasniewski et al., "Microbiota dysbiosis is associated with HPV-induced cervical carcinogenesis," Oncology Letters, vol. 16, No. 6, Sep. 26, 2018, pp. 7035-7047.
Lam et al., "Gene3D: expanding the utility of domain assignments," Nucleic Acids Research, vol. 44, No. D1, Nov. 17, 2015, pp. D404-D409.
Langmead et al., "Fast gapped-read alignment with Bowtie 2," Nature Methods, vol. 9, No. 4, Mar. 4, 2012, pp. 357-359.
Langmead et al., "Ultrafast and memory-efficient alignment of short DNA sequences to the human genome," Genome Biology, vol. 10, No. R25, Mar. 4, 2009, 10 pages.
Letunic et al., "SMART: recent updates, new developments and status in 2015," Nucleic Acids Research, vol. 43, No. D1, Oct. 9, 2014, pp. D257-D260.
Li et al., "An integrated catalog of reference genes in the human gut microbiome," Nature Biotechnology, vol. 32, No. 8, Jul. 6, 2014, pp. 834-841.
Li et al., "Clustering of highly homologous sequences to reduce the size of large protein databases," Bioinformatics Applications Note, vol. 17, No. 3, 2001, pp. 282-283.
Macklaim et al., "At the crossroads of vaginal health and disease, the genome sequence of Lactobacillus iners AB-1," PNAS, vol. 108, Suppl. 1, Mar. 15, 2011, pp. 4688-4695.
Marchler-Bauer et al., "CDD: NCBI's conserved domain database," Nucleic Acids Research, vol. 43, No. D1, Nov. 20, 2014, pp. D222-D226.
Marschalek et al., "Influence of Orally Administered Probiotic Lactobacillus Strains on Vaginal Microbiota in Women with Breast Cancer during Chemotherapy: A Randomized Placebo-Controlled Double-Blinded Pilot Study," Breast Care, vol. 12, Oct. 27, 2017, pp. 335-339.
Motevaseli et al., "The Effect of Lactobacillus crispatus and Lactobacillus rhamnosusCulture Supernatants on Expression of Autophagy Genes and HPV E6 and E7 Oncogenes in The HeLa Cell Line," Cell Journal, vol. 17, No. 4, Winter 2016, pp. 601-607.
Neve et al., "A collection of breast cancer cell lines for the study of functionally distinct cancer subtypes," Cancer Cell, Dec. 2006, vol. 10, No. 6, pp. 515-527.
Nikolskaya et al., "PIRSF Family Classification System for Protein Functional and Evolutionary Analysis," Evolutionary Bioinformatics, Research Article, Jan. 1, 2006, 13 pages.
Norenhag et al., "The vaginal microbiota, human papillomavirus and cervical dysplasia: a systematic review and network meta-analysis," BJOG, vol. 127, Jul. 17, 2019, pp. 171-180.
Notredame et al., "T-Coffee: A Novel Method for Fast and Accurate Multiple Sequence Alignment," Journal of Molecular Biology, vol. 302, Jul. 10, 2000, pp. 205-217.
Nunn et al., "Enhanced Trapping of HIV-1 by Human Cervicovaginal Mucus Is Associated with Lactobacillus crispatus-Dominant Microbiota," mBio, vol. 6, No. 5, Sep. 2015, 9 pages.
Pedruzzi et al., "HAMAP in 2015: updates to the protein family classification and annotation system," Nucleic Acids Research, vol. 43, No. D1, Oct. 27, 2014, pp. D1064-D1070.
Peng et al., "IDBA-UD: a de novo assembler for single-cell and metagenomic sequencing data with highly uneven depth," Bioinformatics, vol. 28, No. 11, Apr. 11, 2012, pp. 1420-1428.
Potenza et al., "MobiDB 2.0: an improved database of intrinsically disordered and mobile proteins," Nucleic Acids Research, vol. 43, No. D1, Oct. 31, 2014, pp. D315-D320.
Pybus et al., "Evidence for a Commensal, Symbiotic Relationship between Gardnerella vaginalis and Prevotella bivia Involving Ammonia: Potential Significance for Bacterial Vaginosis," Journal of Infectious Diseases, vol. 175, Aug. 21, 1996, pp. 406-413.
Qin et al., "A human gut microbial gene catalogue established by metagenomic sequencing," Nature, vol. 464, Mar. 4, 2010, pp. 59-65.
Quast et al., "The SILVA ribosomal RNA gene database project: improved data processing and web-based tools ," Nucleic Acids Research, vol. 41, No. D1, Nov. 27, 2012, pp. D590-D596.
Ravel et al., "Vaginal microbiome of reproductive-age women," PNAS, vol. 108, Suppl. 1, Mar. 15, 2011, pp. 4680-4687.
Riley et al., "Using Sybil for interactive comparative genomics of microbes on the web," Bioinformatics, vol. 28, No. 2, Nov. 24, 2011, pp. 160-166.
Segata et al., "Metagenomic microbial community profiling using unique clade-specific marker genes," Nature Methods, vol. 9, No. 8, Jun. 10, 2012, pp. 811-814.
Shannon et al., "Association of HPV Infection and clearance with cervicovaginal immunology and the vaginal microbiota," vol. 10, No. 5 Jan. 25, 2017, pp. 1310-1319.
Sigrist et al., "Prosite: A documented database using patterns and profiles as motif descriptors," Briefings in Bioinformatics, vol. 3, No. 3, Sep. 2002, pp. 265-274.
Tanenbaum et al., "The JCVI standard operating procedure for annotating prokaryotic metagenomic shotgun sequencing data," Standards in Genomic Sciences, vol. 2, 2010, pp. 229-237.
Tatusov et al., "The COG database: a tool for genome-scale analysis of protein functions and evolution," Nucleic Acids Research, vol. 28, No. 1, Jan. 1, 2000, pp. 33-36.
Tettelin et al., "Genome analysis of multiple pathogenic isolates of *Streptococcus agalactiae*: Implications for the microbial "pan-genome"," PNAS, vol. 102, No. 39, Sep. 27, 2005, pp. 13950-13955.
Yang et al., "Role of Lactobacillus in cervical cancer," Cancer Management and Research, vol. 10, May 16, 2018, pp. 1219-1229.
Zhu et al., "Ab initio gene identification in metagenomic sequences," Nucleic Acids Research, vol. 38, No. 12, Apr. 19, 2010, 15 pages.
International Search Report and Written Opinion for International (PCT) Patent Application No. PCT/US2020/55752, dated Mar. 31, 2021, 19 pages.
Official Action for U.S. Appl. No. 16/800,702, dated May 5, 2020, 7 pages. Restriction Requirement.
Official Action for U.S. Appl. No. 16/800,702, dated Aug. 17, 2020, 32 pages.
Notice of Allowance for U.S. Appl. No. 16/800,702, dated Jan. 1, 2021, 19 pages.
Official Action for U.S. Appl. No. 16/917,661, dated Aug. 17, 2020, 29 pages.
Official Action for U.S. Appl. No. 16/917,661, dated Nov. 4, 2020, 26 pages.
Notice of Allowance for U.S. Appl. No. 16/917,661, dated Dec. 9, 2020, 9 pages.
Official Action for U.S. Appl. No. 17/223,754, dated Jun. 17, 2021, 10 pages.

* cited by examiner

MICROBIOME-BASED INFORMED METHOD TO FORMULATE LIVE BIOTHERAPEUTICS

CROSS-REFERENCE TO RELATED APPLICATION

This application is a divisional of U.S. patent application Ser. No. 16/917,661, filed 30 Jun. 2020 ("the '661 application"), which is a continuation-in-part of U.S. patent application Ser. No. 16/800,702, filed 25 Feb. 2020, which claims the benefit of priority under 35 U.S.C. § 119(e) to U.S. Provisional Patent Application 62/915,852, filed 16 Oct. 2019 ("the '852 application"), and U.S. Provisional Patent Application 62/972,243, filed 10 Feb. 2020 ("the '243 application"). The '661 application also claims priority under 35 U.S.C. § 119(e) to the '852 application and the '243 application. The entireties of all of the above applications are incorporated herein by reference.

FIELD OF THE INVENTION

The present invention relates generally to methods for formulating and/or using live biotherapeutics, and specifically to methods for treating a patient with a live biotherapeutic formulation based on differences between a gene-specific characterization of the patient's microbiome and a reference gene catalog of a human microbiome.

BACKGROUND OF THE INVENTION

The microbial communities that inhabit the human body play critical roles in the maintenance of health, and dysfunction of these communities is often associated with disease. Taxonomic profiling of the human microbiome via 16S rRNA gene amplicon sequencing has provided critical insight into the potential role of the microbiota in a wide array of common diseases, including (among others) bacterial vaginosis, Crohn's disease, and psoriasis, but such profiling routinely falls short of describing the etiology of these diseases. This drawback may be due to the fact that, while 16S rRNA gene sequencing can provide species-level taxonomic profiles of a community, it does not describe the genes or metabolic functions that are encoded in the constituents' genomes. This is an important distinction because strains of a bacterial species often exhibit substantial diversity in gene content, such that their genomes harbor sets of accessory genes whose presence is variable. It is therefore difficult, if not impossible, to infer the complete function of a microbial species in an environment using only their 16S rRNA gene sequence. As a consequence, to investigate the role of the human microbiome in health and disease, particular emphasis must be placed on describing the gene content and expression of these microbial communities.

Metagenomic and metatranscriptomic profiling are emerging approaches aimed at characterizing the gene content and expression of microbial communities. Results from these approaches have led to increased appreciation for the important role microbial communities play in human health and disease. Despite the rapid development and increased throughput of sequencing technologies, however, current knowledge of the genetic and functional diversity of human microbial communities is still limited. This is due, at least in part, to a lack of resources necessary for the analysis of these massive datasets; de novo assembly of metagenomic or metatranscriptomic datasets typically requires substantial computational resources and complicates integration of metagenomic and metatranscriptomic data.

Accurate, high-resolution mapping of metagenomic or metatranscriptomic data against a comprehensive and curated gene database is an alternative analytical strategy that is less computationally demanding, prone to fewer errors, and provides a standard point of reference for comparison of these data. Development of such curated databases is crucial to furthering understanding of the structure and function of microbial communities. In recent years, international initiatives such as MetaHit, the NIH-funded Human Microbiome Project (HMP), and the International Human Microbiome Consortium (IHMC) have been established to generate the resources necessary to enable investigations of the human microbiome, including large reference taxonomic surveys and metagenomic datasets. While multiple 16S rRNA gene catalogs exist, there are relatively few curated resources for referencing metagenomes and metatranscriptomes, and those that do exist focus only on the gut microbiome of either humans or animal model species.

Furthermore, it has been hypothesized that allelic differences in certain genes in the human microbiota may be associated with health or disease, and such allelic differences may thus be useful as selection criteria and/or biomarkers for identification of suitable probiotic strains for use in live biotherapeutic formulations. However, the difficulty of generating gene-specific characterizations of a person's microbiome and a reference gene catalog of a human microbiome have, to date, limited the ability of investigators to discover and exploit such gene-specific health outcomes to formulate live biotherapeutics.

There is thus a need in the art for methods for creating reference gene catalogs for microbiomes of human body sites other than the gut, such as the oral cavity, the skin, and the vagina. There is a further need in the art for methods for formulating and administering live biotherapeutic formulations based on such reference gene catalogs.

SUMMARY OF THE INVENTION

Microbiome studies have become increasingly sophisticated with the rapid advancement of sequencing throughput and the associated decrease in sequencing cost. However, identifying features that drive correlations between the microbiome and health using multi-omics sequencing data remains challenging. This is due, in part, to difficulties in analyzing and integrating the complex metagenomic and metatranscriptomic data now common to microbiome studies. A scalable tool that provides a comprehensive characterization of such multi-omics data is therefore highly desired. Reference gene catalogs generated according to the present invention can be large microbiome databases designed to fulfill such research needs for investigations of microbiomes and their relation to health, e.g. the vaginal microbiome and its relation to reproductive and urogenital health in women. In summary, reference gene catalogs generated according to the present invention may provide any one or more of the following advantages and benefits relative to the solutions of the prior art: (i) comprehensive breadth, including previously observed community types, species, and even fungi and viruses; (ii) a gene-specific design that enables the integration of functional and taxonomic characterization of the metagenomic and metatranscriptomic data originating from the same sample; (iii) a high scalability and low memory requirement; (iv) a high sensitivity that affords characterization of the gene content of low-abundance bacteria; (v) an easy-to-use framework from which to evaluate gene richness and within-species diversity.

Reference gene catalogs generated according to the present invention can contain a multitude of non-redundant genes that can be identified from metagenomes and bacterial isolates. These non-redundant genes can also be clustered into orthologous groups, e.g. vaginal orthologous groups (VOGs) when the microbiome being investigated is the vaginal microbiome, using a memory-efficient network-based algorithm that handles node connectivity in high-dimensionality space. This approach to identifying orthologous protein sequences allows for great flexibility because it does not rely on a single sequence similarity cutoff value. These families of orthologs can assist the development of a mechanistic understanding of these proteins and how they relate to health. For example, the *L. crispatus* pullulanase (pulA) has recently been identified, characterized, and shown to encode an enzyme with amylase activity, which likely allows the species to degrade host glycogen in the vaginal environment. Using the methods of the present invention, the present inventors have been able to identify pullulanase domain-containing proteins in 37 other vaginal taxa, including *G. vaginalis, L. iners*, and *P. timonensis*, providing insight into the breadth of vaginal bacteria that may be capable of degrading host glycogen. In this way, the methods and systems of the present invention can facilitate knowledge retrieval, hypothesis generation, future experimental validation, and the development of novel and/or tailored gene-specific live biotherapeutics for administration to a patient in need thereof.

Using the methods and systems of the present invention, the intraspecies diversity present within individual microbial communities, e.g. individual vaginal microbial communities, can be identified and characterized. Populations of bacterial species in, for example, vaginal communities likely comprise multiple strains. Previous studies of the vaginal microbiome have largely treated these species as singular genotypes, although some more recent studies have examined intraspecies diversity in these communities. Intraspecies diversity is important because it is likely to influence many properties of the communities, including their temporal stability and resilience and their relationship to host health. However, intraspecies diversity is difficult to detect using typical assembly-based metagenomic analysis strategies, which are notoriously ill-suited for resolving strains of the same species. The methods and systems of the present invention can be a more suitable tool for characterizing intraspecies diversity because they are built to contain the non-redundant pangenomes of most species common to the microbial environment, e.g. the vagina. Strict mapping of sequence reads against reference gene catalogs generated according to the present invention provides an accurate and sensitive way of identifying the aggregated non-redundant genes that belong to each species in a metagenome, and it is expressly contemplated that the methods and systems of the present invention may enable future investigations of intraspecies diversity, and leveraging of such intraspecies diversity (e.g. by formulating live biotherapeutics to regulate and/or maintain a degree of intraspecies diversity associated with health), in microbial communities including but not limited to the vaginal microbial community.

Methods and systems of the present invention can be used to determine not only the identity and characteristics of intraspecies diversity, but also the structure thereof. As described in the non-limiting Examples that follow, vaginal metagenomes derived from the microbiota from different subjects contain related sets of species-specific non-redundant genes. Without wishing to be bound by any particular theory, it is believed that these clusters of samples with shared gene content represent similar collectives of strains, which the present inventors term "metagenomic subspecies," and it is expected that, given their shared gene content, these metagenomic subspecies might also share phenotypic characteristics. As a result, live biotherapeutics can be formulated that include, or exclude, one or more identified metagenomic subspecies to provide, or avoid, an identified effect of the metagenomic subspecies on the health of the microbial environment, e.g. the vaginal microbial environment, and by extension the host.

One advantage and benefit of the present invention is its usefulness to generate reference gene catalogs that are both central repositories and highly scalable tools for fast, accurate characterization of a microbiome, e.g. a vaginal microbiome. The methods and systems of the present invention may be particularly useful for users with limited computational skills, a large volume of sequencing data, and/or limited computing infrastructure. In particular, the metagenome-metatranscriptome data integration enabled by the gene-specific design of the methods and systems of the invention provides a powerful approach to determine the expression patterns of microbial functions, and in doing so to characterize contextualized complex mechanisms of host-microbiota interactions in microbial communities, e.g. vaginal communities. This feature makes possible the meta-analysis of microbiome features and the quantitative integration of findings from multiple studies, which helps alleviate the common issue of confounding gene copy number that has been a major challenge in analyzing meta-transcriptomic datasets to date. It is also anticipated that the methods and systems of the present invention may be used to process metaproteomic datasets when that practice becomes common and easily accessible. Each of the protein sequences of each gene could be used to map peptides obtained from metaproteomic pipelines. It is also expressly contemplated that the methods and systems of the present invention may be useful to identify nucleotide variants within a gene—which will further facilitate understanding of within-species diversity and change in a microbial ecosystem, e.g. a vaginal ecosystem, and enable even more selective and/or targeted formulation of live biotherapeutics—and embodiments incorporating this capability are within the scope of the present invention. Furthermore, the methods and systems of the present invention are useful to generate reference gene catalogs including gene sequences of non-bacterial microbes, e.g. viral and fungal gene sequences, providing a more complete understanding of the microbial community of interest.

These and other advantages will be apparent from the disclosure contained herein.

For purposes of further disclosure and to comply with applicable written description and enablement requirements, the following references generally relate to systems and methods for formulation and administration of live biotherapeutics, and are hereby incorporated by reference in their entireties:

Vivien Pybus and Andrew B. Onderdonk, "Evidence for a commensal, symbiotic relationship between *Gardnerella vaginalis* and *Prevotella bivia* involving ammonia: potential significance for bacterial vaginosis," 175(2) *Journal of Infectious Diseases* 406 (February 1997) (hereinafter "Pybus").

T. K. Attwood et al., "The PRINTS protein fingerprint database in its fifth year," 26(1) *Nucleic Acids Research* 304 (January 1998) (hereinafter "Attwood").

Roman L. Tatusov et al., "The COG database: a tool for genome-scale analysis of protein functions and evolution," 28(1) *Nucleic Acids Research* 33 (January 2000) (hereinafter "Tatusov").

Christian J. A. Sigrist et al., "PROSITE: a documented database using patterns and profiles as motif descriptors," 3(3) *Briefings in Bioinformatics* 265 (September 2002) (hereinafter "Sigrist").

Daniel H. Haft et al., "The TIGRFAMs database of protein families," 31(1) *Nucleic Acids Research* 371 (January 2003) (hereinafter "Haft").

Catherine Bru et al., "The ProDom database of protein domain families: more emphasis on 3D," 33(S1) *Nucleic Acids Research* D212 (January 2005) (hereinafter "Bru").

Anastasia N. Nikolskaya et al., "PIRSF family classification system for protein functional and evolutionary analysis," 2 *Evolutionary Bioinformatics* 197 (January 2006) (hereinafter "Nikolskaya").

Sarah Hunter et al., "InterPro: the integrative protein signature database," 37(S1) *Nucleic Acids Research* D211 (January 2009) (hereinafter "Hunter").

David M. Tanenbaum et al., "The JCVI standard operating procedure for annotating prokaryotic metagenomic shotgun sequencing data," 2 *Standards in Genomic Sciences* 229 (April 2010) (hereinafter "Tanenbaum").

PCT Application Publication 2010/079991, entitled "Vector for treatment vaccine for stable and constitutive high-expression cervical cancer and recombinant *Lactobacillus* transformed by the same," published 18 Nov. 2010 to Sung et al.

Minoru Kanehisa et al., "KEGG for integration and interpretation of large-scale molecular data sets," 40(D1) *Nucleic Acids Research* D109 (January 2012) (hereinafter "Kanehisa").

U.S. Pat. No. 8,846,027, entitled "Compositions for the vaginal and oral administration of *Lactobacillus* and uses thereof," issued 30 Sep. 2014 to Kiss et al.

Ivica Letunic et al., "SMART: recent updates, new developments and status in 2015," 43(D1) *Nucleic Acids Research* D257 (January 2015) (hereinafter "Letunic").

Ivo Pedruzzi et al., "HAMAP in 2015: updates to the protein family classification and annotation system," 43(D1) *Nucleic Acids Research* D1064 (January 2015) (hereinafter "Pedruzzi").

Emilio Potenza et al., "MobiDB 2.0: an improved database of intrinsically disordered and mobile proteins," 43(D1) *Nucleic Acids Research* D315 (January 2015) (hereinafter "Potenza").

PCT Application Publication 2015/173693, entitled "Compositions containing boric acid and a mixture of *Lactobacillus*," published 19 Nov. 2015 to de Seta et al.

Robert D. Finn et al., "The Pfam protein families database: towards a more sustainable future," 44(D1) *Nucleic Acids Research* D279 (January 2016) (hereinafter "Finn").

Jaime Huerta-Cepas et al., "eggNOG 4.5: a hierarchical orthology framework with improved functional annotations for eukaryotic, prokaryotic and viral sequences," 44(D1) *Nucleic Acids Research* D286 (January 2016) (hereinafter "Huerta-Cepas").

Su Datt Lam et al., "Gene3D: expanding the utility of domain assignments," 44(D1) *Nucleic Acids Research* D404 (January 2016) (hereinafter "Lam").

Elahe Motevaseli et al., "The effect of *Lactobacillus crispatus* and *Lactobacillus rhamnosus* culture supernatants on expression of autophagy genes and HPV E6 and E7 oncogenes in the HeLa cell line," 17(4) *Cell Journal* 601 (January 2016).

PCT Application Publication 2016/121865, entitled "Lactic-acid-bacteria-containing composition, oral pharmaceutical composition for treating HPV infection and/or HPV-associated tumors, and mucosal immunity-inducing agent," published 4 Aug. 2016 to Kawana et al.

B. Shannon et al., "Association of HPV infection and clearance with cervicovaginal immunology and the vaginal microbiota," 10(5) *Mucosal Immunology* 1310 (September 2017).

U.S. Patent Application Publication 2018/0114592, entitled "Method and system for characterizing allergy-related conditions associated with microorganisms," published 26 Apr. 2018 to Apte et al.

Xi Yang et al., "Role of *Lactobacillus* in cervical cancer," 2018(10) *Cancer Management and Research* 1219 (May 2018).

Wojciech Kwasniewski et al., "Microbiota dysbiosis is associated with HPV-induced cervical carcinogenesis," 16(6) *Oncology Letters* 7035 (December 2018).

U.S. Pat. No. 10,169,541, entitled "Method and system for characterizing skin related conditions," issued 1 Jan. 2019 to Apte et al.

U.S. Pat. No. 10,246,753, entitled "Method and system for characterizing mouth-associated conditions," issued 2 Apr. 2019 to Apte et al.

J. Norenhag et al., "The vaginal microbiota, human papillomavirus and cervical dysplasia: a systematic review and network meta-analysis," 127(2) *BJOG* 171 (January 2020).

As used herein, "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B, and C together.

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The embodiments and configurations described herein are neither complete nor exhaustive. As will be appreciated, other embodiments of the invention are possible utilizing, alone or in combination, one or more of the features set forth above or described in detail below.

DETAILED DESCRIPTION OF THE INVENTION

Figure 1:
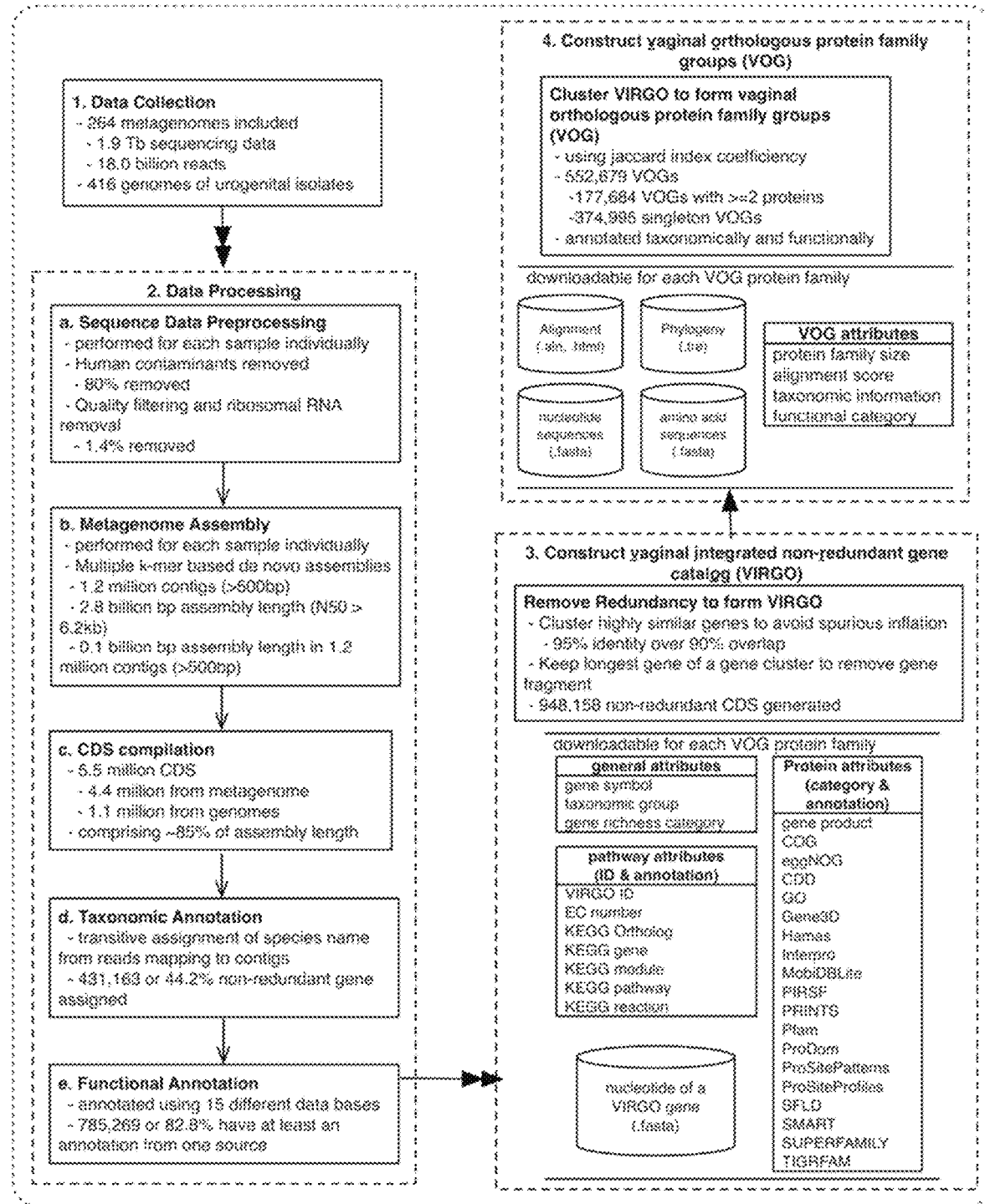
FIG. 1 is a flowchart illustrating a data processing and integration scheme for the construction of a human vaginal integrated non-redundant gene catalog (VIRGO).

Unless defined otherwise, all technical and scientific terms used herein have the same meaning as is commonly understood by one of ordinary skill in the art. All patents, applications, published applications, and other publications to which reference is made herein are incorporated by reference in their entirety. In the event that there is a plurality of definitions for a term herein, the definition provided in the Brief Summary of the Invention prevails unless otherwise stated.

"CRISPR" (Clustered Regularly Interspaced Short Palindromic Repeats) loci refers to certain genetic loci encoding components of DNA cleavage systems, for example, used by bacterial and archaeal cells to destroy foreign DNA. A CRISPR locus can consist of a CRISPR array, comprising short direct repeats (CRISPR repeats) separated by short variable DNA sequences (called spacers), which can be flanked by diverse Cas (CRISPR-associated) genes. The CRISPR-Cas system, an example of a pathway that was unknown to science prior to the DNA sequencing era, is now understood to confer bacteria and archaea with acquired immunity against phage and viruses. Intensive research over the past decade has uncovered the biochemistry of this system. CRISPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CRISPR-Cas are streamlined versions in which a single Cas protein bound to RNA is responsible for binding to and cleavage of a targeted sequence. The programmable nature of these minimal systems has facilitated their use as a versatile technology that is revolutionizing the field of genome manipulation.

As used herein, an "effector" or "effector protein" is a protein that encompasses an activity including recognizing, binding to, and/or cleaving or nicking a polynucleotide target. An effector, or effector protein, may also be an endonuclease. The "effector complex" of a CRISPR system includes Cas proteins involved in crRNA and target recognition and binding. Some of the component Cas proteins may additionally comprise domains involved in target polynucleotide cleavage.

The term "Cas protein" refers to a polypeptide encoded by a Cas (CRISPR-associated) gene. A Cas protein includes proteins encoded by a gene in a cas locus, and include adaptation molecules as well as interference molecules. An interference molecule of a bacterial adaptive immunity complex includes endonucleases. A Cas endonuclease described herein comprises one or more nuclease domains. A Cas endonuclease includes but is not limited to: the novel Cas-alpha protein disclosed herein, a Cas9 protein, a Cpf1 (Cas12) protein, a C2c1 protein, a C2c2 protein, a C2c3 protein, Cas3, Cas3-HD, Cas 5, Cas7, Cas8, Cas10, or combinations or complexes of these. A Cas protein may be a "Cas endonuclease" or "Cas effector protein", that when in complex with a suitable polynucleotide component, is capable of recognizing, binding to, and optionally nicking or cleaving all or part of a specific polynucleotide target sequence.

CRISPR-Cas systems have been classified according to sequence and structural analysis of components. Multiple CRISPR/Cas systems have been described including Class 1 systems, with multisubunit effector complexes (comprising type I, type III, and type IV), and Class 2 systems, with single protein effectors (comprising type II, type V, and type VI). A CRISPR-Cas system comprises, at a minimum, a CRISPR RNA (crRNA) molecule and at least one CRISPR-associated (Cas) protein to form crRNA ribonucleoprotein (crRNP) effector complexes. CRISPR-Cas loci comprise an array of identical repeats interspersed with DNA-targeting spacers that encode the crRNA components and an operon-like unit of cas genes encoding the Cas protein components. The resulting ribonucleoprotein complex recognizes a polynucleotide in a sequence-specific manner. The crRNA serves as a guide RNA for sequence specific binding of the effector (protein or complex) to double strand DNA sequences, by forming base pairs with the complementary DNA strand while displacing the noncomplementary strand to form a so called R-loop. RNA transcripts of CRISPR loci (pre-crRNA) are cleaved specifically in the repeat sequences by CRISPR associated (Cas) endoribonucleases in type I and type III systems or by RNase III in type II systems. The number of CRISPR-associated genes at a given CRISPR locus can vary between species.

Different cas genes that encode proteins with different domains are present in different CRISPR systems. The cas operon comprises genes that encode for one or more effector endonucleases, as well as other Cas proteins. Some domains may serve more than one purpose, for example Cas9 comprises domains for endonuclease functionality as well as for target cleavage, among others. The Cas endonuclease is guided by a single CRISPR RNA (crRNA) through direct RNA-DNA base-pairing to recognize a DNA target site that is in close vicinity to a protospacer adjacent motif (PAM). Class I CRISPR-Cas systems comprise Types I, III, and IV. A characteristic feature of Class I systems is the presence of an effector endonuclease complex instead of a single protein. A Cascade complex comprises a RNA recognition motif (RRM) and a nucleic acid-binding domain that is the core fold of the diverse RAMP (Repeat-Associated Mysterious Proteins) protein superfamily.

Type I CRISPR-Cas systems comprise a complex of effector proteins, termed Cascade (CRISPR-associated complex for antiviral defense) comprising at a minimum Cas5 and Cas7. The effector complex functions together with a single CRISPR RNA (crRNA) and Cas3 to defend against invading viral DNA. Type I systems are divided into seven subtypes.

Type III CRISPR-Cas systems, comprising a plurality of cas7 genes, target either ssRNA or ssDNA, and function as either an RNase as well as a target RNA-activated DNA nuclease. Type IV systems, although comprising typical type I cas5 and cas7 domains in addition to a cas8-like domain, may lack the CRISPR array that is characteristic of most other CRISPR-Cas systems.

Class II CRISPR-Cas systems comprise Types II, V, and VI. A characteristic feature of Class II systems is the presence of a single Cas effector protein instead of an effector complex. Types II and V Cas proteins comprise an RuvC endonuclease domain that adopts the RNase H fold. Type II CRISPR/Cas systems employ a crRNA and tracrRNA (trans-activating CRISPR RNA) to guide the Cas endonuclease to its DNA target. The crRNA comprises a spacer region complementary to one strand of the double strand DNA target and a region that base pairs with the tracrRNA (trans-activating CRISPR RNA) forming a RNA duplex that directs the Cas endonuclease to cleave the DNA target, leaving a blunt end. Spacers are acquired through a not fully understood process involving Cas1 and Cas2 proteins. Type II CRISPR/Cas loci typically comprise cas1 and cas2 genes in addition to the cas9 gene. Type II CRISR-Cas loci can encode a tracrRNA, which is partially complementary to the repeats within the respective CRISPR array, and can comprise other proteins such as Csn1 and Csn2. The presence of cas9 in the vicinity of cas1 and cas2 genes is the hallmark of type II loci. Type V CRISPR/Cas systems comprise a single Cas endonuclease, including Cpf1 (Cas12) that is an active RNA-guided endonuclease that does not necessarily require the additional trans-activating CRISPR (tracr) RNA for target cleavage, unlike Cas9. Type VI CRISPR-Cas systems comprise a cas13 gene that encodes a nuclease with two HEPN (Higher Eukaryotes and Prokaryotes Nucleotide-binding) domains but no HNH or RuvC domains, and are not dependent upon tracrRNA activity. The majority of HEPN domains comprise conserved motifs that constitute a metal-independent endoRNase active site. Because of this feature, it is thought that type VI systems act on RNA targets instead of the DNA targets that are common to other CRISPR-Cas systems.

To comply with written description and enablement requirements, incorporated herein by the following references are the following patent publications: 2014/0349405 to Sontheimer; 2014/0377278 to Elinav; 2014/0068797 to Doudna; 20200190494 to Hou, et. al.; and 2020/0199555 to Zhang.

It is one aspect of the present invention to provide a method for ameliorating, treating, or preventing a malignancy in a female human subject, comprising (a) generating a gene-specific characterization, at an intraspecies level, of the subject's vaginal microbial community; (b) comparing the gene-specific characterization to a reference gene catalog of the human vaginal microbiome, wherein the reference gene catalog comprises at least one metagenome or single-strain genome associated with a healthy microbiome; (c) identifying, based on the comparison of step (b), a deficiency or excess of at least one bacterial strain in the subject's vaginal microbial community; (d) formulating a remedial live biotherapeutic formulation, comprising bacteria adapted to remedy the deficiency or excess of the at least one bacterial strain in the subject's vaginal microbial community; and (e) administering the remedial live biotherapeutic formulation to the subject.

In embodiments, the malignancy may be a cancer of the female genitourinary system.

In embodiments, the bacteria adapted to remedy the deficiency or excess of the at least one bacterial strain in the subject's vaginal microbial community may comprise a selected strain or consortium of strains of a bacterial species selected from the group consisting of *Lactobacillus crispatus, Lactobacillus gasseri*, and *Lactobacillus jensenii*. The bacteria may, but need not, comprise at least one of (i) *Lactobacillus crispatus* bacteria configured to express, carry, harbor, or encode at least one of the asparagine synthase B (asnB) gene of SEQ ID NO: 1 and the asparagine synthase B (asnB) gene of SEQ ID NO: 2; and (ii) *Lactobacillus crispatus* bacteria containing an asparagine synthase B (asnB) gene encoding at least one of a polypeptide of SEQ ID NO: 3 and a polypeptide of SEQ ID NO: 4.

In embodiments, step (a) may comprise at least one sub-step selected from the group consisting of (i) preprocessing sequence data for each of one or more samples by at least one of removing human contaminants from a sample, quality-filtering, and removing ribosomal RNA; (ii) assembling at least one metagenome from each of one or more samples by executing a procedure to generate one or more nucleotide based de novo assemblies; (iii) compiling coding DNA sequences (CDSs); (iv) applying at least one taxonomic annotation by transitive assignment of species name from reads mapping to contigs; and (v) applying at least one functional annotation using annotations from one or more functional databases.

In embodiments, the live biotherapeutic formulation may further comprise a pharmaceutically acceptable carrier.

In embodiments, the live biotherapeutic formulation may further comprise an agent adapted to reduce or remove free ammonia from the vaginal environment.

It is another aspect of the present invention to provide a method for achieving an improvement in the vaginal health of a female human subject, comprising (a) generating a gene-specific characterization, at an intraspecies level, of the subject's vaginal microbial community; (b) comparing the gene-specific characterization to a reference gene catalog of the human vaginal microbiome, wherein the reference gene catalog comprises at least one metagenome or single-strain genome associated with a healthy microbiome; (c) identifying, based on the comparison of step (b), a deficiency or excess of at least one bacterial strain in the subject's vaginal microbial community; (d) formulating a remedial live biotherapeutic formulation, comprising bacteria adapted to remedy the deficiency or excess of the at least one bacterial strain in the subject's vaginal microbial community; and (e) administering the remedial live biotherapeutic formulation to the subject, wherein the improvement is selected from the group consisting of treating bacterial vaginosis in the subject, decreasing ammonia in the vaginal environment of the subject, reducing inflammation in the subject, preventing overgrowth of at least one of *Gardnerella vaginalis* and *Prevotella* spp. in the vagina of the subject, and combinations thereof.

In embodiments, the bacteria adapted to remedy the deficiency or excess of the at least one bacterial strain in the subject's vaginal microbial community may comprise a selected strain or consortium of strains of a bacterial species selected from the group consisting of *Lactobacillus crispatus, Lactobacillus gasseri*, and *Lactobacillus jensenii*. The bacteria may, but need not, comprise at least one of (i) *Lactobacillus crispatus* bacteria configured to express at least one of the asparagine synthase B (asnB) gene of SEQ ID NO: 1 and the asparagine synthase B (asnB) gene of SEQ ID NO: 2; and (ii) *Lactobacillus crispatus* bacteria containing an asparagine synthase B (asnB) gene encoding at least one of a polypeptide of SEQ ID NO: 3 and a polypeptide of SEQ ID NO: 4. The bacteria may, but need not, comprise *Lactobacillus crispatus*, and the preselected strain or consortium of strains may, but need not, comprise at least one strain selected from the group consisting of LUCA111, LUCA011, LUCA015, LUCA009, LUCA102, LUCA006, LUCA059, LUCA103, and LUCA008.

In embodiments, step (a) may comprise at least one sub-step selected from the group consisting of (i) preprocessing sequence data for each of one or more samples by at least one of removing human contaminants from a sample, quality-filtering, and removing ribosomal RNA; (ii) assembling at least one metagenome from each of one or more samples by executing a procedure to generate one or more nucleotide based de novo assemblies; (iii) compiling coding DNA sequences (CDSs); (iv) applying at least one taxonomic annotation by transitive assignment of species name from reads mapping to contigs; and (v) applying at least one functional annotation using annotations from one or more functional databases.

In embodiments, the live biotherapeutic formulation may further comprise a pharmaceutically acceptable carrier.

In embodiments, the live biotherapeutic formulation further may further comprise an agent adapted to reduce or remove free ammonia from the vaginal environment.

It is another aspect of the present invention to provide a live biotherapeutic formulation adapted for administration to the vaginal environment of a female human subject, comprising one or more of (i) *Lactobacillus crispatus* bacteria configured to express at least one of the asparagine synthase B (asnB) gene of SEQ ID NO: 1 and the asparagine synthase B (asnB) gene of SEQ ID NO: 2; (ii) *Lactobacillus crispatus* bacteria containing an asparagine synthase B (asnB) gene encoding at least one of a polypeptide of SEQ ID NO: 3 and a polypeptide of SEQ ID NO: 4; and (iii) a preselected strain or consortium of strains of *Lactobacillus crispatus*, comprising at least one strain selected from the group consisting of LUCA111, LUCA011, LUCA015, LUCA009, LUCA102, LUCA006, LUCA059, LUCA103, and LUCA008.

In embodiments, the live biotherapeutic formulation may further comprise a redox potential control agent.

In embodiments, the live biotherapeutic formulation may further comprise a pH buffer configured to maintain a healthy pH of the vaginal environment.

In embodiments, the live biotherapeutic formulation may further comprise an antimicrobial agent.

In embodiments, the live biotherapeutic formulation may further comprise a growth promoter.

In embodiments, the live biotherapeutic formulation may further comprise a pharmaceutically acceptable carrier.

The present invention provides methods and systems for constructing reference gene catalogs for human microbiomes, i.e. integrated and comprehensive resources to establish taxonomic and functional profiling of microbiomes, e.g. vaginal microbiomes, from metagenomic and metatranscriptomic datasets. In the case of vaginal microbiomes specifically, such reference gene catalogs can be constructed using a combination of metagenomes and urogenital bacterial isolate genomes. The genes identified in these data can be further clustered into vaginal orthologous groups (VOGs), providing a catalog of functional protein families common to vaginal microbiomes. The gene catalog can be curated with taxonomic assignments as well as functional features using diverse protein databases. Importantly, the present inventors have shown that reference gene catalogs constructed according to the present invention can provide greater than 95% coverage of the human vaginal microbiome and be applicable to populations from North America, Africa, and Asia. The methods and systems of the present invention can thus provide a comprehensive reference repository and a convenient cataloging tool for fast and accurate characterization of vaginal metagenomes and metatranscriptomes. The reference gene catalogs produced according to the present invention can be compilations of vaginal bacterial species pangenomes, creating a vaginal "meta-pan-genome." Methods and systems of the present invention can be further used to characterize the amount of intraspecies diversity present in individual vaginal communities; whereas previous characterization of these communities using either 16S rRNA gene taxonomic profiling or assembly-based metagenomic analyses has failed to resolve this diversity, the present inventors have shown that vaginal communities contain far more intraspecies diversity than originally expected. This insight challenges the conventional idea that the vaginal microbiota are dominated by one strain, or even one species, of *Lactobacillus*, and has major implications for the ecology of these otherwise low-diversity bacterial communities. Ultimately, reference gene catalogs produced according to the present invention and their associated analytical frameworks can facilitate and standardize the analysis and interpretation of large metagenomic and metatranscriptomic datasets, thus expanding understanding of the role of vaginal microbial communities in health and disease.

Methods for constructing or generating a reference gene catalog according to the present invention generally comprise at least one data collection step, at least one data processing step, and at least one redundancy removal step. In the at least one data collection step, metagenomes and/or isolate genomes from one or more microbial communities are generally obtained and/or newly sequenced. The at least one data processing step generally comprises at least one step or sub-step selected from the following: (i) preprocessing sequence data for each of one or more samples, e.g. by removing human contaminants from a sample, quality-filtering, and/or removing ribosomal RNA; (ii) assembling at least one metagenome from each of one or more samples, e.g. by executing a procedure to generate one or more nucleotide based de novo assemblies; (iii) compiling coding DNA sequences (CDSs); (iv) taxonomic annotation, e.g. by transitive assignment of species name from reads mapping to contigs; and (v) functional annotation, e.g. using annotations from one or more functional databases. The at least one redundancy removal step generally comprises at least one of clustering highly similar genes to avoid spurious inflation and keeping the longest gene of a gene cluster to remove gene fragments. In embodiments, the method may further comprise at least one orthologous protein family grouping step, which generally comprises clustering genes using Jaccard index coefficiency. Reference gene catalogs generated according to the present invention generally include, for each orthologous protein family group, at least one type of information selected from the following: (i) general attributes (e.g. gene symbol, taxonomic group, gene richness category); (ii) pathway attributes (e.g. ID and annotation); (iii) protein attributes (e.g. category and annotation); (iv) orthologous group attributes (e.g. protein family size, alignment score, taxonomic information, functional category); (v) alignment(s); (vi) phylogeny or phylogenies; (vii) nucleotide sequence(s); and (ix) amino acid sequence(s).

The present invention also provides methods and systems for treating a human patient with a live biotherapeutic formulation. In general, such methods include constructing a reference gene catalog by the methods described herein, comparing a gene-specific characterization of a microbiome of the patient with the reference gene catalog, identifying a deficiency or overabundance of a bacterial strain in the patient's microbial community relative to the reference gene catalog, formulating a remedial live biotherapeutic formulation comprising bacteria selected to address the deficiency or overabundance, and administering the remedial live biotherapeutic to the patient.

The methods and systems of the present invention allow users not only to obtain greater insight into human-associated microbial communities, but to translate these insights into clinical biomarkers and treatments, e.g. live biotherapeutics. Deeper understandings of the complex mechanisms of host-microbiota interactions require the integration of multi-omics data. The present invention provides for the generation of reference gene catalogs that serve as a central reference database and an analytical framework to enable the efficient and accurate characterization of the microbial gene content of a microbiome, e.g. the human vaginal microbiome, and allows for the integrated analysis of metagenomic and metatranscriptomic data. The present invention further provides a gene-specific approach to describe the structure of microbial communities, e.g. vaginal microbial communities, with fine-scale variation at the intraspecies level. Such insights into intraspecies diversity within a microbial community are far beyond the capabilities of current genome references and investigation tools. The present invention also facilitates the analysis of multi-omics data now common to microbiome studies; provides comprehensive insight into community membership, function, and ecological perspective of a microbiome, e.g. the vaginal microbiome; and is useful to formulate gene-specific, and therefore more targeted and effective, live biotherapeutics.

Microbiome studies have become increasingly sophisticated with the rapid advancement of sequencing throughput and the associated decrease in sequencing cost. However, identifying features that drive correlations between the microbiome and health using multi-omics sequencing data remains challenging. This is due, in part, to difficulties in analyzing and integrating the complex metagenomic and metatranscriptomic data now common to microbiome studies. A scalable tool that provides a comprehensive characterization of such multi-omics data is therefore highly desired. Reference gene catalogs generated according to the present invention can be large microbiome databases designed to fulfill such research needs for investigations of microbiomes and their relation to health, e.g. the vaginal microbiome and its relation to reproductive and urogenital health in women. In summary, reference gene catalogs generated according to the present invention may provide any one or more of the following advantages and benefits relative to the solutions of the prior art: (i) comprehensive breadth, including previously observed community types, species, and even fungi and viruses; (ii) a gene-specific design that enables the integration of functional and taxonomic characterization of the metagenomic and metatranscriptomic data originating from the same sample; (iii) a high scalability and low memory requirement; (iv) a high sensitivity that affords characterization of the gene content of low-abundance bacteria; (v) an easy-to-use framework from which to evaluate gene richness and within-species diversity.

Reference gene catalogs generated according to the present invention can contain a multitude of non-redundant genes that can be identified from metagenomes and bacterial isolates. These non-redundant genes can also be clustered into orthologous groups, e.g. vaginal orthologous groups (VOGs) when the microbiome being investigated is the vaginal microbiome, using a memory-efficient network-based algorithm that handles node connectivity in high-dimensionality space. This approach to identifying orthologous protein sequences allows for great flexibility because it does not rely on a single sequence similarity cutoff value. These families of orthologs can assist the development of a mechanistic understanding of these proteins and how they relate to health. For example, the *L. crispatus* pullulanase (pulA) has recently been identified, characterized, and shown to encode an enzyme with amylase activity, which likely allows the species to degrade host glycogen in the vaginal environment. Using the methods of the present invention, the present inventors have been able to identify pullulanase domain-containing proteins in 37 other vaginal taxa, including *G. vaginalis, L. iners*, and *P. timonensis*, providing insight into the breadth of vaginal bacteria that may be capable of degrading host glycogen. In this way, the methods and systems of the present invention can facilitate knowledge retrieval, hypothesis generation, future experimental validation, and the development of novel and/or tailored gene-specific live biotherapeutics for administration to a patient in need thereof.

Using the methods and systems of the present invention, the intraspecies diversity present within individual microbial communities, e.g. individual vaginal microbial communities, can be identified and characterized. Populations of bacterial species in, for example, vaginal communities likely comprise multiple strains. Previous studies of the vaginal microbiome have largely treated these species as singular genotypes, although some more recent studies have examined intraspecies diversity in these communities. Intraspecies diversity is important because it is likely to influence many properties of the communities, including their temporal stability and resilience and their relationship to host health. However, intraspecies diversity is difficult to detect using typical assembly-based metagenomic analysis strategies, which are notoriously ill-suited for resolving strains of the same species. The methods and systems of the present invention can be a more suitable tool for characterizing intraspecies diversity because they are built to contain the non-redundant pangenomes of most species common to the microbial environment, e.g. the vagina. Strict mapping of sequence reads against reference gene catalogs generated according to the present invention provides an accurate and sensitive way of identifying the aggregated non-redundant genes that belong to each species in a metagenome, and it is expressly contemplated that the methods and systems of the present invention may enable future investigations of intraspecies diversity, and leveraging of such intraspecies diversity (e.g. by formulating live biotherapeutics to regulate and/or maintain a degree of intraspecies diversity associated with health), in microbial communities including but not limited to the vaginal microbial community.

Methods and systems of the present invention can be used to determine not only the identity and characteristics of intraspecies diversity, but also the structure thereof. As described in the non-limiting Examples that follow, vaginal metagenomes from different subjects contain related sets of species-specific non-redundant genes. Without wishing to be bound by any particular theory, it is believed that these clusters of samples with shared gene content represent similar collectives of strains, which the present inventors term "metagenomic subspecies," and it is expected that, given their shared gene content, these metagenomic subspecies might also share phenotypic characteristics. As a result, live biotherapeutics can be formulated that include, or exclude, one or more identified metagenomic subspecies to provide, or avoid, an identified effect of the metagenomic subspecies on the health of the microbial environment, e.g. the vaginal microbial environment.

One advantage and benefit of the present invention is its usefulness to generate reference gene catalogs that are both central repositories and highly scalable tools for fast, accurate characterization of a microbiome, e.g. a vaginal microbiome. The methods and systems of the present invention may be particularly useful for users with limited computational skills, a large volume of sequencing data, and/or limited computing infrastructure. In particular, the metagenome-metatranscriptome data integration enabled by the gene-specific design of the methods and systems of the invention provides a powerful approach to determine the expression patterns of microbial functions, and in doing so to characterize contextualized complex mechanisms of host-microbiota interactions in microbial communities, e.g. vaginal communities. This feature makes possible the meta-analysis of microbiome features and the quantitative integration of findings from multiple studies, which helps alleviate the common issue of confounding gene copy number that has been a major challenge in analyzing meta-transcriptomic datasets to date. It is also anticipated that the methods and systems of the present invention may be used to process metaproteomic datasets when that practice becomes common and easily accessible. Each of the protein sequences of each gene could be used to map peptides obtained from metaproteomic pipelines. It is also expressly contemplated that the methods and systems of the present invention may be useful to identify nucleotide variants within a gene—which will further facilitate understanding of within-species diversity and change in a microbial ecosystem, e.g. a vaginal ecosystem, and enable even more selective and/or targeted formulation of live biotherapeutics—and embodiments incorporating this capability are within the scope of the present invention. Furthermore, the methods and systems of the present invention are useful to generate reference gene catalogs including gene sequences of non-bacterial microbes, e.g. viral and fungal gene sequences, providing a more complete understanding of the microbial community of interest.

Formulation of Live Biotherapeutics for Vaginal Microbiome Treatment

In reproductive-age women, *Lactobacillus* spp. are characteristic of an optimal vaginal microbiota. *Lactobacillus* spp. produce bacteriocins to suppress pathogenic growth of certain bacteria, as well as lactic acid. Lactic acid lowers the vaginal pH to around 4.5 or less, hampering the survival of other bacteria.

The vaginal microbiome differs in important ways from other microbiomes; for example, while an optimal gut microbiome is a highly diverse, high-biomass microbial community, an optimal vaginal microbiome is characterized by low bacterial diversity often dominated by one species of *Lactobacillus*. Specifically, previous metataxonomic studies utilizing 16S rRNA gene sequencing analysis have revealed that there are five major Community State Types (CSTs) of the vaginal microbiome, of which four are dominated by one species of *Lactobacillus*: CST I (dominated by *L. crispatus*), CST II (dominated by *L. gasseri*), CST III (dominated by *L. iners*), and CST V (dominated by *L. jensenii*). CST IV, however, which includes the vaginal microbiomes of about 25% of women, is characterized by a relative dearth of *Lactobacillus* spp. Low abundance of *Lactobacillus* in the vaginal microbiome is associated with increased risk for severe adverse gynecologic and obstetric outcomes. Adverse gynecologic outcomes associated with low *Lactobacillus* abundance include, but are not limited to, acquisition of sexually transmitted infections (STIs) (including human immunodeficiency virus (HIV), chlamydia, gonorrhea, herpes simplex virus (HSV), and human papillomavirus (HPV)), bacterial vaginosis (the most frequently cited cause of vaginal discharge and malodor), yeast infection, urinary tract infection (UTI), and pelvic inflammatory disease (PID). Adverse obstetric outcomes associated with low *Lactobacillus* abundance include, but are not limited to, preterm delivery and low birth weight, infertility, stillbirth, premature rupture of membranes (PROM), postpartum and post-abortal endometritis, amniotic fluid infection, and chorioamnionitis. *Lactobacillus* spp. are thus key to reproductive and gynecological health, and not all CSTs are equally protective; CST IV is associated with high risk to these and other adverse health outcomes, and CST III is suboptimal compared to CSTs I, II, and V (see, e.g., Vonetta L. Edwards et al., "The cervicovaginal microbiota-host interaction modulates *Chlamydia trachomatis* infection," 10(4) *mBio* e01548-19 (August 2019), and Kenetta L. Nunn et al., "Enhanced trapping of HIV-1 by human cervicovaginal mucus is associated with *Lactobacillus crispatus*-dominant microbiota," 6(5) *mBio* e01084-15 (October 2015), the entireties of both of which are incorporated herein by reference). Moreover, it is known that the distribution of vaginal microbiome CSTs varies with race; for example, 40.5% of black women and 38.1% of Hispanic women harbor a CST IV vaginal microbiome, compared to 19.8% of Asian women and 10.3% of white women.

While several proposed solutions to the restoration and maintenance of vaginal microbiota associated with positive health outcomes exist, these proposed solutions suffer from several drawbacks. The selection of strains used in the formulation of live biotherapeutics (LBPs) is empiric and is based on criteria such as adhesion or antimicrobial production, but little or no information is available on the women and the microbiota from which the strains were cultured. Often, the LBPs comprise strains of a particular species (e.g. *L. crispatus, L. gasseri,* or *L. jensenii*) that are not typically found in the vaginal microbiome. In these approaches, there is no ecological or scientific rationale for strain selection, and the efficacy of LBPs formulated according to these approaches has yet to be demonstrated as superior to current drug treatments.

A list of selected currently available LBPs for maintenance of the vaginal microbiome is given in Table 1.

TABLE 1

| Formulation name | Ingredients |
|---|---|
| PHYSIOFLOR | *L. crispatus* IP 174178 |
| KRAMEGIN | *L. acidophilus* + *Krameria triandra* plant extract + lactic acid |
| GYNOFLOR | *L. acidophilus* KS400 + estriol |
| LACTAGYN | *L. acidophilus, L. rhamnosus, S. thermophilus, L. delbrueckii* subsp. *Bulgaricus* |
| GYNOPHILUS | *L. casei rhamnosus* Lcr35 |
| ACTICAND | *L. fermentum* LF10 + *L. acidophilus* LA02 |
| ESTROMINERAL PROBIOGEL | *L. fermentum* LF10 + *L. plantarum* LP02 |
| ECOVAG | *L. gasseri* EB01-DSM 14869 + *L. rhamnosus* Lbp PB01-DSM 14870 |
| GYNO-CANESFLOR | *L. plantarum* P17630 |
| FEMILAC | *L. rhamnosus* + *L. delbrueckii* + *L. acidophilus* + *S. thermophilus* |
| SYNBIO GIN | *L. rhamnosus* IMC 501 + *L. paracasei* IMC 502 |
| GYNOPHILUS LP | *L. rhamnosus* Lcr35 regenerans |
| ECOLOGIC FEMI+ | *B. bifidum* W28 + *L. acidophilus* W70 + *L. helveticus* W74 + *L. brevis* W63 |
| FLORISIA | *L. brevis* CD2 + *L. salivarius* subsp. *salicinius* FV2 + *L. plantarum* FV9 |
| LACTIN V | *L. crispatus* CTV-05 |
| RC-14/GR-1 | *L. fermentum* RC-14 + *L. rhamnosus* GR-1 |
| DAYE PROBIOTIC | *L. plantarum* GLP3 |

Even CST alone, while more informative than its gut microbiome equivalent, lacks the functional information necessary to formulate an effective LBP, because the particular strain of *Lactobacillus* spp. is the driver of functional specificity and certain strains are better than others.

Reference gene catalogs of genes in the vaginal microbiome, generated according to the methods and systems of the present invention, overcome these drawbacks and allow for the formulation of much more effective LBPs. Particularly, because the reference gene catalogs of the present invention are comprehensive, have broad application to different populations and ethnicities, and reveal extensive within-woman intraspecies diversity, those who wish to formulate LBPs for restoration of the vaginal microbiota can identify multiple strains of a species that may contribute to (or detract from) the health of the vaginal environment and provide functional redundancy that guarantees stability of the species in situ in the vaginal environment. The present invention allows reference gene catalogs created thereby to be leveraged to rationally design and select one or more bacterial strains, or a mixture ("consortium") thereof, as therapeutics.

The present inventors have identified certain features that may be desired in LBP formulations to provide stability and resilience to the vaginal microbiome. By way of non-limiting example, not all *L. crispatus* strains are equally beneficial to host health; vaginal microbiota dominated by *L. crispatus* can be highly stable, but can also lack resilience upon disturbance, such as the use of a lubricant or sexual intercourse. It is desirable to provide vaginal microbiota dominated by stable and resilient *L. crispatus*, but prior to the present invention, no known characteristics could predict the stability of *L. crispatus*.

EXAMPLES

The invention is further described by way of the following non-limiting Examples.

Example 1: Construction of Human Vaginal Non-Redundant Gene Catalog

This Example describes the construction of a human vaginal non-redundant gene catalog (VIRGO) according to the methods of the present invention.

211 newly sequenced vaginal datasets and 53 vaginal datasets downloaded from the HMP data repository were obtained. Genome sequences of deposited urogenital bacterial isolates were downloaded from multiple databases, including GenBank, Integrated Microbial Genomes & Microbiomes (IMG/M), and the HMP referencing genome database. After removing duplicate genomes under the same strain names, genomes of 322 urogenital bacterial strains representing 152 bacterial species were included.

The 211 newly sequenced metagenomes were generated as follows: whole genomic DNA was extracted from 300 µL aliquots of vaginal ESwab re-suspended into 1 mL of Amies transport medium and preserved at −80° C. Cells were then lysed using a combination of enzymatic digestion (including mutanolysin, lysostaphin, and lysozyme treatment) and mechanical disruption, followed by proteinase K, SDS, and bead beating steps. DNA extraction and concentration qualification were performed according to the procedures described in Jacques Ravel et al., "Vaginal microbiome of reproductive-age women," 108(S1) *Proceeding of the National Academy of Sciences* 4680 (June 2010) (hereinafter "Ravel"), the entirety of which is incorporated herein by reference. The shotgun metagenomic sequence libraries were constructed from the extracted DNA using Illumina Nextera XT kits and sequences on an Illumina HiSeq 2500 platform (150 bp paired end mode, eight samples per lane).

The metatranscriptomes used to demonstrate the use of the present invention for the analysis of community-wide gene expression were obtained from RNA extracted from vaginal swabs stored in 2 mL of Amies Transport Medium-RNAlater solution (50/50 by volume) archived at −80° C. A total of 500 µL of ice-cold PBS was added to 1,000 µL of that solution and spun at 8,000 g for 10 minutes. The pellet was resuspended in 500 µL of ice-cold RNase-free PBS with 10 µL of β-mercaptoethanol. The suspension was transferred to Lysis Matrix B tubes containing 100 µL of 10% SDS and 500 µL of acid phenol and bead beaten using a FastPrep instrument for 45 seconds at 5.5 m/s. The aqueous phase was mixed with 250 µL of acid phenol and 250 µL of a 24:1 solution of chloroform and isoamyl alcohol. The aqueous layer was again transferred to a fresh tube and mixed with 500 µL of the chloroform/isoamyl alcohol solution. For each part by volume of resulting aqueous solution, 0.1 parts of 3 M sodium acetate, 0.01 parts of 5 mg/mL glycogen, and three parts of 100% ethanol were added. The mixture was incubated at −20° C. overnight to precipitate the nucleic acids. After centrifugation at 13,400 g for 30 minutes at 4° C., the resulting pellet was washed, dried, and dissolved in 100 µL of DEPC-treated water. Carryover DNA was removed by (1) treating twice with Turbo DNase free at two half-hour intervals, according to the manufacturer's protocol, for rigorous DNase treatment, and (2) purifying twice using gDNA-eliminator columns before and after DNase treatment, followed by RNeasy column purification. PCR was further conducted using 16S rRNA primer 27F (5'-AGAGTTTGATCCTGGCTCAG-3') and 534R (5'-CAT-TACCGCGGCTGCTGG-3') to confirm DNA removal. The quality of extracted RNA was checked using an Agilent 2100 Expert Bioanalyzer Nano chip. Ribosomal RNA removal was performed with a combined Gram-positive, Gram-negative, and human/mouse/rat Ribo-Zero rRNA Removal Kit, according to the manufacturer's protocol. The resulting RNA was purified using a Zymo Research RNA Clean & Concentrator-5 column kit. Final RNA quality was checked using an Agilent RNA 6000 Expert Bioanalyzer Pico chip. Sequencing libraries were prepared using an Illumina TruSeq RNA sample prep kit with a modification to the manufacturer's protocol: cDNA was purified between enzymatic reactions and library size selection was performed with AMPure XT beads. Library sequencing was performed using the Illumina HiSeq 2500 platform (150 bp paired end mode, eight samples per lane).

Multiple bioinformatics pre-processing steps were applied to the raw shotgun metagenomic sequence datasets, including (1) eliminating all human sequence reads (including human rRNA LSU/SSU sequence reads) using BMTagger v3.101 against a standard human genome reference (GRCh37.p5, as described in Deanna M. Church et al., "Modernizing reference genome assemblies," 9(7) *PLos Biology* e1001091 (July 2011), the entirety of which is incorporated herein by reference); (2) in silico microbial rRNA sequence reads depletion by aligning all reads using Bowtie v1 (as described in Ben Langmead et al., "Ultrafast and memory-efficient alignment of short DNA sequences to the human genome," 10 *Genome Biology* R25 (March 2009), the entirety of which is incorporated herein by reference) against the SILVA PARC ribosomal-subunit sequence database (as described in Christian Quast et al., "The SILVA ribosomal RNA gene database project: improved data processing and web-based tools," 41(D1) *Nucleic Acids Research* D590 (January 2013), the entirety of which is incorporated herein by reference) to eliminate misassemblies of these repeated regions, after each of which steps the paired reads were removed; and (3) stringent quality control using Trimmomatic v0.36 (as described in Anthony M. Bolger et al., "Trimmomatic: a flexible trimmer for Illumina sequence data," 30(15) *Bioinformatics* 2114 (August 2014), the entirety of which is incorporated herein by reference), in which the Illumina adapters were excised, reads were trimmed using a 4 bp sliding window with an average quality score threshold of Q15, and reads containing any ambiguous bases were removed. MetaPhlAn v2 (as described in Nicola Segata et al., "Metagenomic microbial community profiling using unique Glade-specific marker genes," 9 *Nature Methods* 811 (June 2012), the entirety of which is incorporated herein by reference) was subsequently used to establish taxonomic profiles after these pre-processing steps. Samples were then clustered in community state types (CSTs) using taxa abundance tables and the Jensen-Shannon divergence metrics as described in Ravel. The 264 vaginal metagenomes were then assembled using IDBA-UD v1.0 (as described in Yu Peng et al., "IDBA-UD: a de novo assembly for single-cell and metagenomic sequencing data with highly uneven depth," 28(11) *Bioinformatics* 1420 (June 2012), the entirety of which is incorporated herein by reference) with a k-value range of 20 to 100.

Genes were called on the resulting contigs using MetageneMark v3.25 (as described in Wenhan Zhu et al., "Ab initio gene identification in metagenomic sequences," 38(12) *Nucleic Acids Research* e132 (July 2010), the entirety of which is incorporated herein by reference) to predict coding DNA sequences (CDSs) with the default settings; FIG. 1 illustrates the method used to identify and cluster CDSs. Metagenomic assemblies contributed about 80% of the CDSs, while the remaining about 20% originated from urogenital bacteria isolate genome sequences. Genes and gene fragments that were at least 99 bp long, with greater than 95% identity over 90% of the shorter gene length, were clustered together by a greedy pairwise comparison implemented in CD-HIT-EST v4.6 (as described in Weizhong Li et al., "Clustering of highly homologous sequences to reduce the size of large protein databases," 17(3) *Bioinformatics* 282 (March 2001), the entirety of which is incorporated herein by reference), according to the clustering procedure and threshold described in Junjie Qin et al., "A human gut microbial gene catalogue established by metagenomic sequencing, 464 *Nature* 59 (March 2010) (hereinafter "Qin"), and Junhua Li et al., "An integrated catalog of reference genes in the human gut microbiome," 32 *Nature Biotechnology* 834 (July 2014), the entireties of both of which are incorporated herein by reference. The gene with the longest length greater than or equal to 99 bp was used as the representative for each cluster of redundant genes. This process afforded the removal of partial genes and eliminated overcalling as unique because of sequencing errors.

A total of 948,158 non-redundant CDSs longer than 99 bp were identified and retained, representing 17.2% of the original 5.5 million CDSs. The newly sequenced vaginal metagenomes used to build VIRGO contributed 12 times more non-redundant genes (634,288 genes) than the HMP vaginal metagenomes (54,500 genes). Combined, the metagenomes contributed twice as many non-redundant genes as urogenital bacterial isolate genome sequences.

Of the approximately 18 billion reads generated for the newly sequenced metagenomes, about 14.4 billion (79.7%) were identified as human sequences and removed, but the present inventors found that vaginal metagenomes dominated by *Lactobacillus* spp. had significantly higher proportions of human sequence reads than those from *Lactobacillus*-deficient metagenomes (88.7% vs. 73.3%, t=−6.6, P<0.001). The newly sequenced metagenomes totaled 1.2 million contigs, with a combine length of 2.8 billion base pairs and an $N_{50}$ of 6.2 kbp. The metagenomic data obtained from the HMP contributed 40,000 contigs, comprising 100 million bp of assembled sequence; the newly sequenced metagenomes provided 19.5 times more assembled length than the HMP vaginal metagenomes.

The MetaPhlAn taxonomic analysis of the metagenomes revealed that the microbial communities contained 312 bacterial species present at a relative abundance of at least 0.01%. Among others, all major vaginal *Lactobacillus* species (*L. crispatus, L. gasseri, L. iners*, and *L. jensenii*), as well as common facultative and strict anaerobic vaginal species (e.g. *Gardnerella vaginalis, Atopobium vaginae, Prevotella amnii, Megasphaera* genomosp, *Mobiluncus mulieris, Mageebacillus indolicus* (BVAB3), and *Veillonella parvula*) were identified in the metagenomes, Even bacteria associated with bacterial vaginosis that are often only present at low abundance—e.g. *Finegoldia magna, Peptoniphilus harei, Peptostreptococcus anaerobius, Mobiluncus curtisii, Peptoniphilus lacrimalis, Anaerococcus tetradius, Ureaplasma urealyticum, Veillonella atypica*, and *Corynebacterium glucuronolyticum*—were represented. The taxonomic profiles of 264 metagenomes encompassed the five vaginal community state types (CSTs) reported in Ravel, with frequencies of 18.9% for CST I, 3.8% for CST II, 20.5% for CST III, 48.5% for CST IV, and 8.3% for CST V. These results highlight the taxonomic breadth of the vaginal bacterial communities included in the construction of VIRGO.

Example 2: Bioinformatics Analysis

This Example demonstrates the comprehensiveness of reference gene catalogs generated according to the present invention.

The comprehensiveness of VIRGO was tested using vaginal metagenomics data from 91 vaginal metagenomes obtained from North American women not included in the construction of VIRGO or sequenced in this study, as well as African and Chinese women, which allowed for determination of the utility of VIRGO to analyze metagenomes from other populations. The sequence reads were first mapped to the VIRGO contigs using Bowtie v2 (parameters—threads 4—sensitive-local -D 10-R 2-N 0-L 22-i 5,1,1.75-k 1—ignore-quals—no-unal, as described in Ben Langmead and Steven L. Salzberg, 9 *Nature Methods* 357 (March 2012), the entirety of which is incorporated herein by reference), according to the criteria described in Qin. Any unmapped reads were compared to the GenBank nt database (as described in NCBI Resource Coordinators, "Database resources of the National Center for Biotechnology Information," 45(Database) *Nucleic Acids Research* D12 (January 2017), the entirety of which is incorporated herein by reference), using BLASTN and an E-value of 1E-10 as cutoff. To annotate BVAB1 genes in VIRGO, BLASTN and an E-value of 1E-10 as cutoff were likewise used, and the matched genes with more than 95% identity over more than 90% of gene length were annotated as BVAB1 genes. To retrieve pullulanase (pulA) genes in VIRGO, conserved protein domain CDD annotation (as described in Aron Marchler-Bauer et al., "CDD: NCBI's conserved domain database," 43(D1) *Nucleic Acids Research* D222 (January 2015) (hereinafter "Marchler-Bauer"), the entirety of which is incorporated herein by reference) was used with keyword "pullulanase." To further demonstrate the comprehensiveness of VIRGO and the fact that VIRGO captures the pangeome of selected species, species-specific metagenome accumulation curves and diversity estimates for the number of non-redundant genes were constructed by rarefaction with 100 bootstraps using R packages iNEXT v2.0 and vegan v2.5-5 (as described in Philip Dixon, "VEGAN, a package of R functions for community ecology," 14(6) *Journal of Vegetation Science* 927 (December 2003), the entirety of which is incorporated herein by reference) for seven species: *A. vaginae*, *G. vaginalis*, *L. crispatus*, *L. gasseri*, *L. iners*, *L. jensenii*, and *P. timonensis*.

Figure 2:
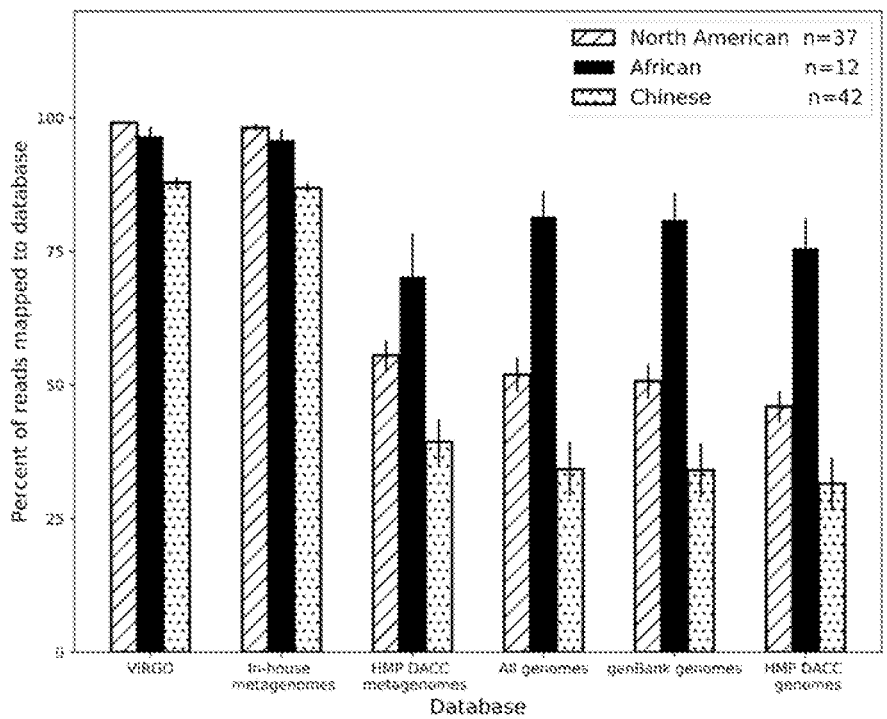
FIG. 2 is a graph of the percentage of vaginal metagenome reads that can be mapped to contigs from various reference data sets.

As illustrated in FIG. 2, more than 99% of the reads from North American metagenomes were able to be mapped to the complete VIRGO dataset, whereas only about 55% of these reads mapped to contigs from the HMP vaginal metagenomes subset. This result indicates a lack of genetic diversity in the HMP vaginal metagenomes, which were derived from highly selected and otherwise healthy women. Further, despite originating from populations not used in the construction of VIRGO, 96% of the reads from African women and 88% of the reads from Chinese women mapped to the complete VIRGO dataset. For these two cohorts 71.7% and 99.9%, respectively, of the reads that failed to map to VIRGO also did not have a match in GenBank.

By including many metagenomes and bacterial isolate genome sequences, each vaginal species' pangenome is represented in VIRGO. The number of non-redundant genes for five of the six species are similar (about 5,000 genes), while for *A. vaginae* the number is roughly twice this amount. These gene counts pale in comparison, however, to the number of non-redundant genes included in VIRGO for *G. vaginalis*, which surpasses 25,000 genes. These results illustrate the comprehensiveness of VIRGO and its broad application to different populations and ethnicities.

Example 3: Taxonomic and Functional Annotation of VIRGO

This Example demonstrates the utility of reference gene catalogs produced according to the present invention to characterize vaginal microbial communities.

Figure 3A:
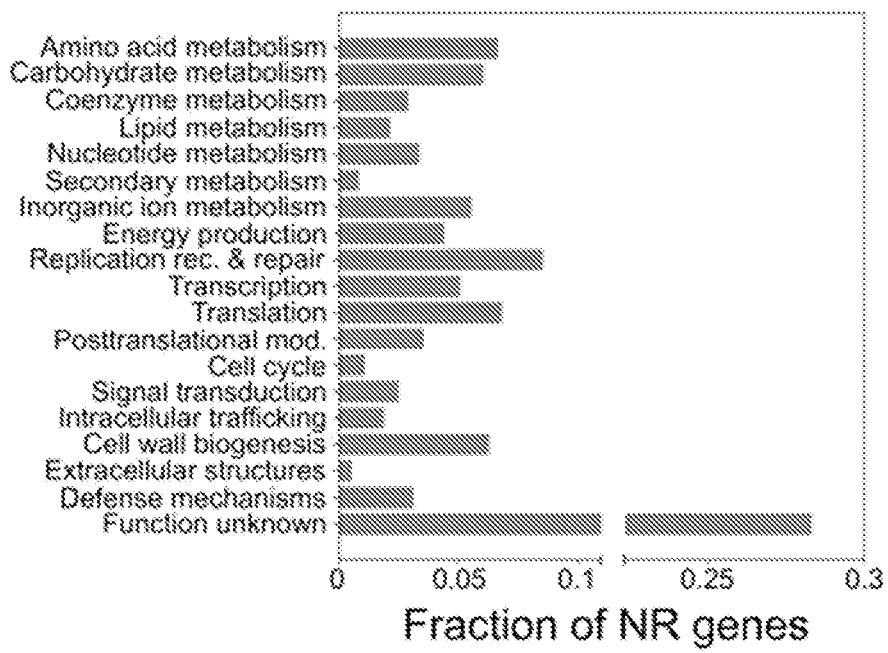
FIG. 3A is a graph of the functional distribution of non-redundant genes in VIRGO.
Figure 3B:
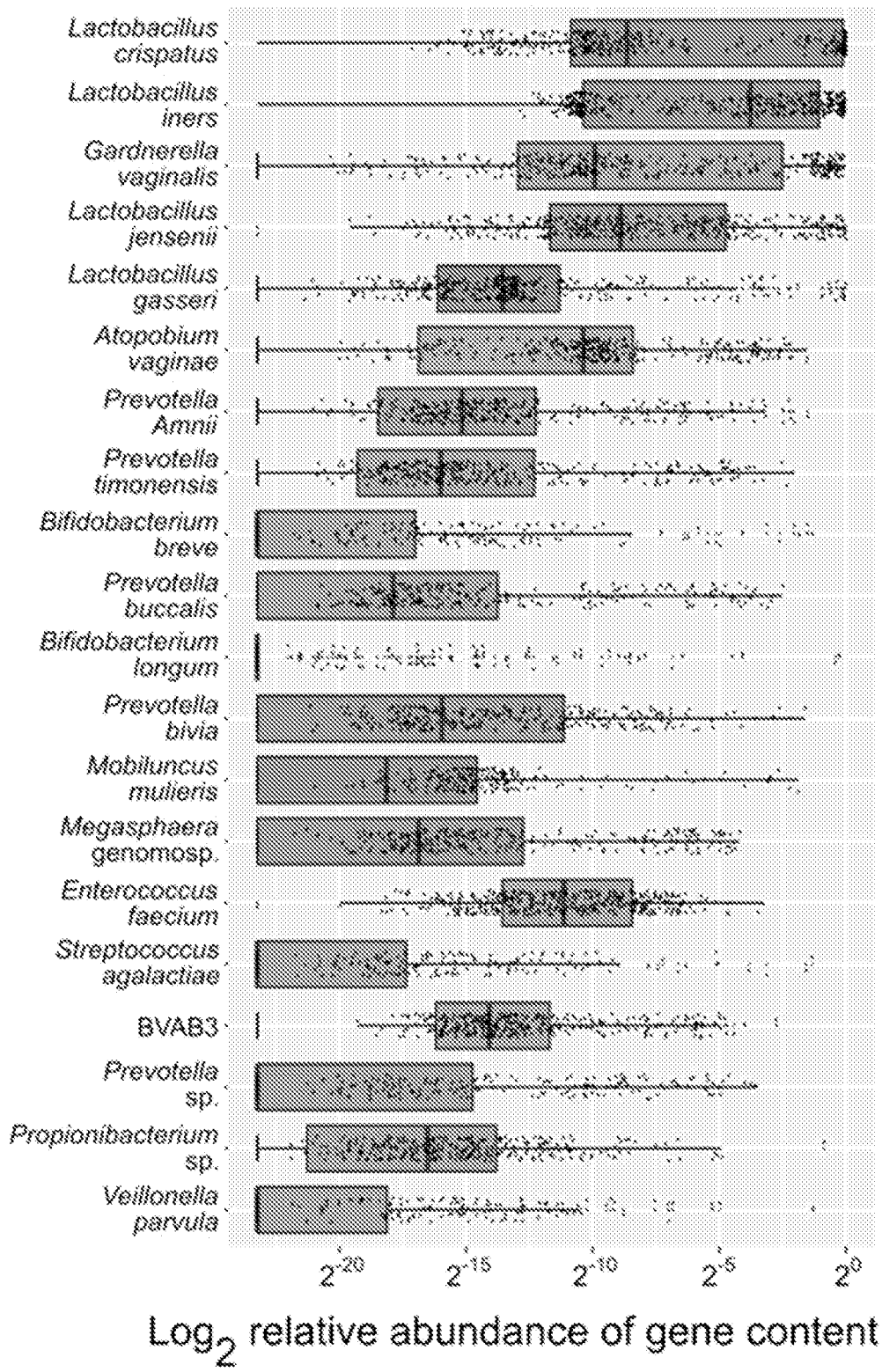
FIG. 3B is a boxplot of the twenty species having the most abundant gene content in VIRGO.

The non-redundant genes of VIRGO were annotated with a rich set of taxonomic and functional information. Genes that originated from an isolate sequence genome were automatically assigned that species name. For metagenomes, taxonomy was assigned to a metagenomic contig by mapping the sequence reads making up that contig to the Integrated Microbial Genomes (IMG) reference database (v400) using Bowtie v1 (parameters: "−1 25—fullref—chunkmbs 512—best—strata −m 20"). A secondary filter was applied so that the total number of mismatches between the read and the reference was less than 35 and the first 25 bp of the read matched the reference. Using the results of this mapping, taxonomy was assigned to all genes encoded on the contig that matched the following four criteria: (1) at least 95% of the reads mapped to the same bacterial species, (2) the remaining 5% of off-target reads did not map to a single species, (3) the contig had at least 2× average coverage and more than 50 reads, and (4) at least 25% of the total length of the contig had reads mapped thereon. These stringent criteria were used to ensure high fidelity of the taxonomic assignments and a low contribution of potentially chimeric contigs. To further diminish the risk of incorporating false taxonomic assignments, the annotations of the contigs belonging to species at low relative abundance in the sample were removed. Genome completeness was estimated as the fractional representation of the genome in the metagenome using BLASTN (minimal overlapping of more than 60% of the shorter sequence and more than 80% sequence similarity). For each metagenome, only taxonomic assignments originating from species with at least 80% representation were incorporated. The genes that showed more than 80% sequence similarity to the non-redundant genes over 60% of query gene length were then assigned. The non-redundant genes in VIRGO were searched against a fungal database that included five vaginal yeast species in 40 genomes using BLASTN, such that a gene must have at least 80% sequence similarity over 60% of overlapping length to be curated. Potential phage genes that may be present in VIRGO were also annotated by searching against phage orthologous groups or prokaryotic virus orthologous groups (version 2016, as described in David M. Kristensen et al., "Orthologous gene clusters and taxon signature genes for viruses of prokaryotes," 195(5) Bacteriology 941 (March 2013), the entirety of which is incorporated herein by reference), using BLASTN and including the genes having more than 80% sequence similarity over 60% of query gene length in annotation. Functional annotations were based on the standard procedure for each of 17 functional databases, including cluster of orthologous groups (COG as described in Tatusov, eggnog (v4.5) as described in Huerta-Cepas, and KEGG as described in Kanehisa), conserved protein domain (CDD as described in Marchler-Bauer, Pfam as described in Finn, ProDom as described in Bru, PROSITE as described in Sigrist, TIGRFAM as described in Haft, and InterPro as described in Hunter), domain architectures (CATH-Gene3D as described in Lam and SMART as described in Letunic), intrinsic protein disorder (MobiDB as described in Potenza), high-quality manual annotation (HAMAP as described in Petruzzi), protein superfamily (PIRSF as described in Nikolskaya), a compendium of protein fingerprints (PRINTS as described in Attwood), and gene product attributes (Gene Ontology and JCVI SOP as described in Tanenbaum). An overview of the eggNOG functions encoded in VIRGO is shown in FIG. 3B.

A total of 445,739 non-redundant genes, comprising 47.0% of VIRGO, were able to be taxonomically annotated. Overall, 271 unique bacterial species were annotated in VIRGO, representing a majority of the described vaginal species. This includes BVAB1, a currently unculturable vaginal species, for which a closed genome and several metagenome-assembled genomes (MAGs) have recently been made available. When stratified by CST, CST IV metagenomes have the smallest proportion (less than 30%) of their gene content taxonomically annotated, compared to about 45% to 50% in *Lactobacillus*-dominated CSTs. The most abundant species based on gene content are shown in FIG. 3C. The curated potential fungal and phage genes were generally present in low abundance (0.17%±0.04% and 0.03%±0.001%, respectively). An additional 10,908 fungal genes and 15,965 phage genes were included.

Overall, 785,268 genes-82.8% of all non-redundant genes—were assigned a functional annotation from at least one source. This gene-rich annotation of the non-redundant gene catalog enables a comprehensive functional characterization of vaginal metagenomes and metatranscriptomes.

Figure 4A:
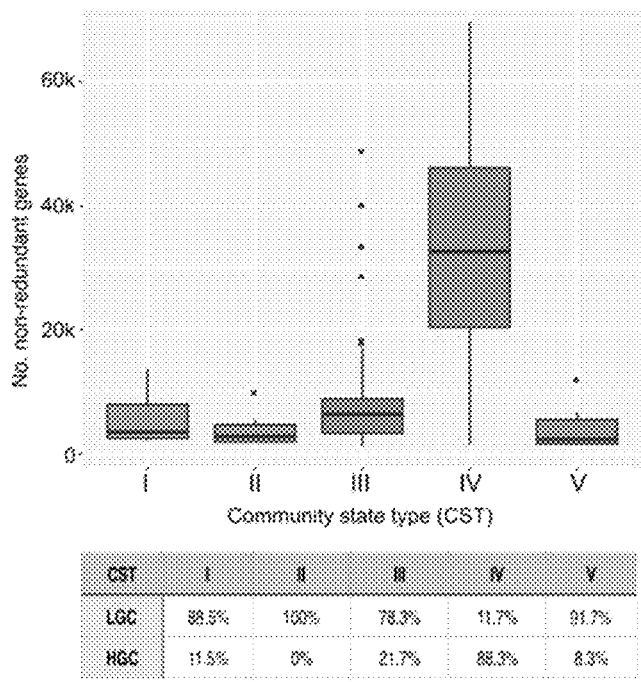
FIG. 4A is a boxplot of the number of non-redundant genes in samples of different community state types (CSTs).
Figure 4B:
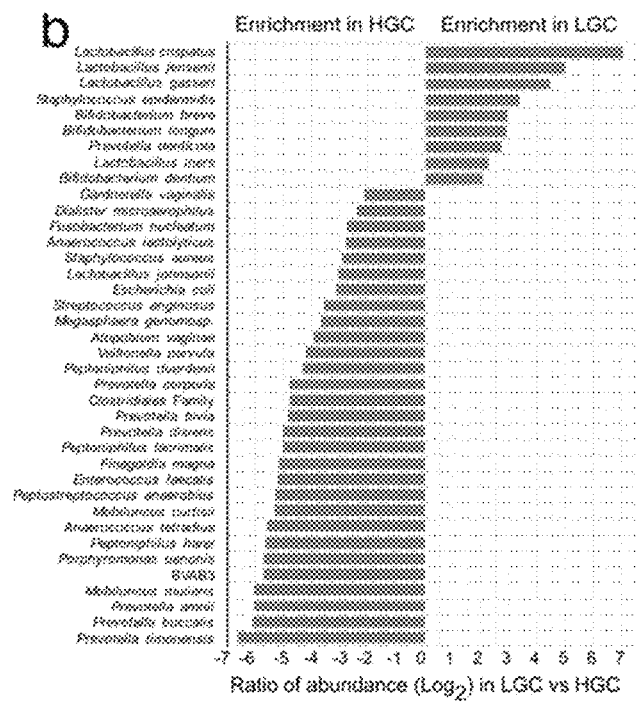
FIG. 4B is a plot of the logy transformed ratio of the abundance of genes of a species in high gene count (HGC) communities to the same abundance in low gene count (LGC) communities.
Figure 5:
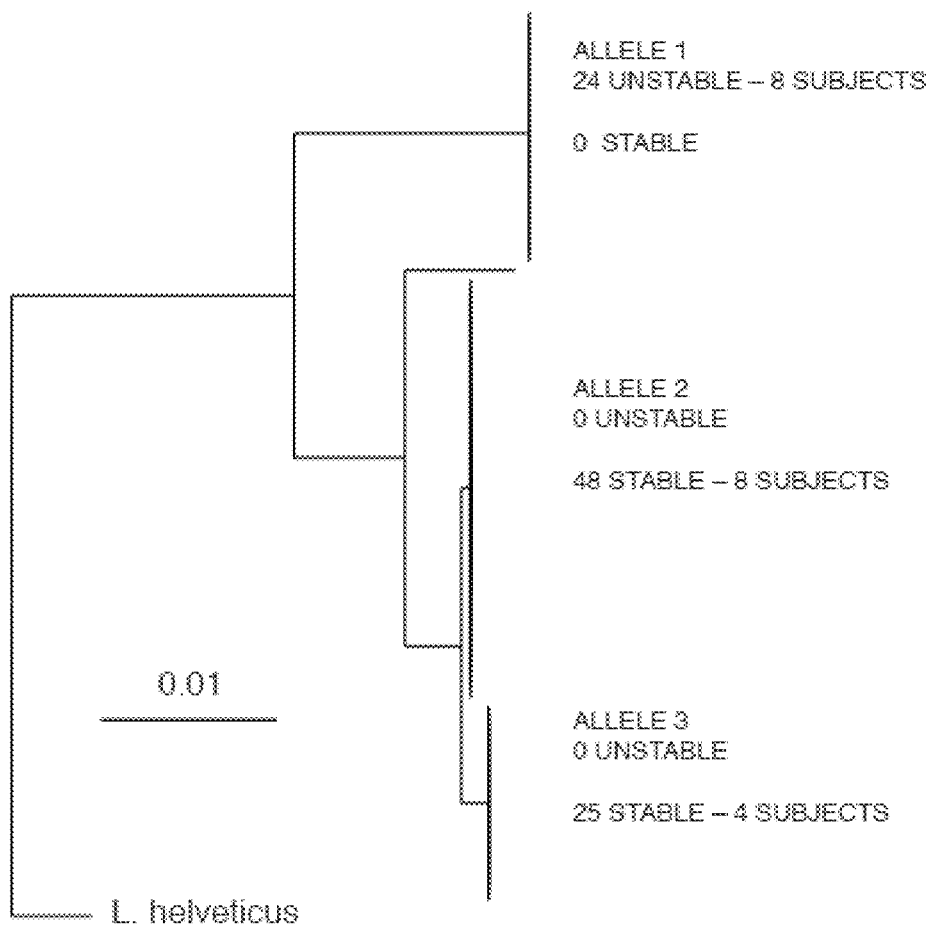
FIG. 5 is a maximum likelihood tree of the *L. crispatus* asparagine synthase B (asnB) gene.

The community gene content, or gene richness, can be characterized as the number of non-redundant genes. As illustrated in FIG. 4A, *Lactobacillus*-dominated communities were typically categorized as low gene count (LGC), as 82.9% of these communities have fewer than 1,000 genes; *Lactobacillus*-deficient communities commonly have high gene count (HGC), in that 88.3% of these communities have more than 1,000 genes. Further, genes of a particular vaginal species can be overrepresented in HGC or LGC vaginal communities (FIG. 4B) with distinct functional makeups. *Lactobacillus* spp., particularly *L. crispatus*, *L. jensenii*, *L. gasseri*, and *L. vaginalis*, were observed to be highly overrepresented in LGC communities. On the other hand, genes belonging to many other species associated with bacterial vaginosis, particularly *P. timonensis, P. buccalis, P. amnii, M. mulieris, Mageeibacillus indolicus, Porphyromonas uenonis, P. harei, Anaerococcus tetradius*, and *M. curtisii*, were overrepresented in HGC communities. These results illustrate that gene richness-based annotations can provide an added dimension to the understanding of the genetic basis of the biological processes that drive vaginal microbiomes.

Example 4: Construction of Vaginal Orthologous Groups for Protein Families

This Example illustrates clustering of genes in reference gene catalogs according to the present invention based on orthology to generate a set of orthologous groups, in this case vaginal orthologous groups (VOGs).

A modified version of a Jaccard clustering method, as previously implemented in David R. Riley et al., "Using Sybil for interactive comparative genomics of microbes on the web," 28(2) *Bioinformatics* 160 (January 2012) (the entirety of which is incorporated herein by reference), was used to cluster genes into VOGs. An all-against-all BLASTP search was performed among the translated coding sequences (CDS) of the non-redundant genes included in VIRGO. The all-against-all BLASTP matches were used to compute a Jaccard similarity coefficient for each pair of translated CDSs, without constraints based on the sample or organism from which it originated. Only BLASTP matches with at least 80% sequence identity, at least 70% overlap, and an E-value of less than 1E-10 were used in the calculation of the Jaccard similarity coefficient. The filtered BLASTP results were then used to define connections between pairs of translated CDSs, resulting in a network graph with the translated CDSs as nodes and their connections as edges. The Jaccard similarity coefficient was then calculated as the number of nodes that had direct connections to the two translated CDSs divided by the total number of nodes that had direct connections to either of the two translated CDSs in the network (intersection divided by union, as described in Jonathan Crabtree et al. "Sybil: methods and software for multiple genome comparison and visualization," in Michael F. Ochs (ed.), Gene Function Analysis 93 (2007), the entirety of which is incorporated herein by reference). A Jaccard cluster (JACs) was defined as a set of translated CDSs whose Jaccard similarity coefficient was at least 0.55. If two translated CDSs from different JACs were reciprocal best matches according to the BLASTP searches, the two JACs were merged and defined as Jaccard orthologous clusters (JOCs). Finally, the alignment program T-Coffee (as described in Cedric Notredame, "T-coffee: a novel method for fast and accurate multiple sequence alignment," 302(1) *Journal of Molecular Biology* 205 (September 2000), the entirety of which is incorporated herein by reference) was used to assess the alignment quality within the JACs and to calculate the alignment score.

The JOCs (orthologous protein families) can be highly conserved (having an alignment score of more than 950) or partially aligned with both conserved and variable regions (having an alignment score of about 300). This result highlights the flexibility of the network-based aggregation algorithm used to recruit both highly similar and distantly related proteins without imposing a single similarity threshold. A total of 617,127 JACs and 552,679 JOCs were generated, of which 177,684 JOCs contained at least two genes while the remaining 374,995 JOCs were singletons, indicating that 38.5% of all VOG proteins are unique.

To demonstrate the utility of VOGs, 32 proteins of the orthologous family encoding vaginolysin, a *G. vaginalis* cholesterol-dependent cytolysin that is key to its pathogenicity as it forms pores in epithelial cells, were retrieved. Using the retrieved alignment, three amino acid variants in an 11-amino acid sequence of domain 4 of vaginolysin were identified. One of the three variants, an alanine-to-valine substitution that is divergent across *G. vaginalis*, had not been reported previously. Thus, VOGs can be mined to understand biological relevance—in this case, potential differences in pore formation activity and possibly cytotoxicity, which can be further investigated and possibly exploited to formulate live biotherapeutics. As another non-limiting example, VOGs were searched using the key phrase "cell surface-associated proteins" and "*L. iners*" and retrieved two protein families, one of which was recognized to have an LPXTG motif while the other harbored the motif YSIRK. Notably, a previous study on staphylococcal proteins suggested that the motifs LPXTG and YSIRK are involved in different biological processes related to surface protein anchoring to the cell wall envelope. The two retrieved protein families are specific to *L. iners* and provide a relevant starting point for further investigation of its adherence and/or formulation of live biotherapeutics leveraging this difference. These results demonstrate how a VOG database generated according to the present invention can be used to explore and exploit more mechanistic understandings of vaginal bacterial communities.

Example 5: Integration of Metagenome and Metatranscriptome Data

This Example illustrates how reference gene catalogs generated according to the present invention enable the characterization and integrative analysis of the abundance of genes and their expression in a microenvironment, in this case the vaginal microenvironment.

A female human subject's vaginal metagenomes and associated metatranscriptomes were analyzed at four time points: prior to (T1), during (T2 and T3), and after (T4) an episode of symptomatic bacterial vaginosis. Unsurprisingly, the expressed functions represented in the metatranscriptomes were often different from the encoded functional makeup of the corresponding metagenomes. VIRGO provided rapid binning of genes by species, which revealed dramatic differences in gene abundance and their transcriptional activity in vaginal species. Prior to the episode of bacterial vaginosis (time point T1), a small proportion (1.5%) of *L. iners* genes were present, but these genes exhibited high expression levels, accounting for over 20% of the metatranscriptome. At the same time point, *L. crispatus* genes made up the majority of the genes present (96.3%) but exhibited low expression levels (34.2% of the metatranscriptome). By contrast, near the end of the episode of bacterial vaginosis (time point T3), *L. crispatus* genes made up a small proportion of the metagenome but were highly transcriptionally active. This increased activity corresponded with *L. crispatus* regaining dominance at T4, following the resolution of the episode of bacterial vaginosis. Notably, the functions encoded by *G. vaginalis* were similar between T2 and T3, but their expression differed between these time points. By enabling this integration of these types of data, reference gene catalogs generated according to the present invention can thus provide a functional understanding of the microbiota, e.g. the vaginal microbiota, and provide insight into the formulation of appropriate live biotherapeutics for the treatment of a particular disease or disorder associated with specific metagenomic and/or metatranscriptomic characteristics.

Example 6: Characterization of Within-Community Intraspecies Diversity

This Example illustrates how reference gene catalogs generated according to the present invention can be used to conduct intraspecies diversity analyses.

Intraspecies diversity analyses were conducted by mapping isolate genome sequences and vaginal metagenomes to VIRGO. The analysis was focused on the seven vaginal species discussed in Example 2 above. A total of 1,507 vaginal metagenomes, including 1,403 metagenomes newly obtained from de-identified vaginal swab and lavage specimens and 76 publicly available metagenomes, were mapped against VIRGO. For each of the seven bacterial species, a presence/absence matrix for the species' non-redundant genes, including the data from the species' isolate genomes and all metagenomes that contained at least 80% of the average number of genes encoded on a genome of that species, was constructed. Comparisons of the number of non-redundant genes present in the species isolate genomes against the metagenomes in which they appeared were conducted using the student t-test. Hierarchical clustering was performed on the Boolean matrix of the species' non-redundant genes using Jaccard clustering implemented in the vegan package in R.

The number of non-redundant genes identified in a metagenome was not found to correlate with the depth sequencing. Most of each species' gene content was recovered even when that species was present at low abundance (less than 1%) in a community. For instance, even though $P.$ $timonensis$ was generally present in low abundance in these metagenomes (mean 4.8%, standard deviation 0.3%, minimum 0.1, maximum 33.8%), the majority of its genome was recovered (2,469±401 CDSs). Similarly high sensitivity was observed in the analysis of the other six selected vaginal species. These results demonstrate the capability of reference gene catalogs generated according to the present invention to characterize the gene content of even low-abundance taxa from metagenomics data.

Using these species-specific gene repertoires, the amount of intraspecies diversity present within an individual woman's vaginal microbiome can be characterized. Because VIRGO (or another reference gene catalog of the invention) comprises the "pangenomes" of each vaginal bacterial species, it can be used to evaluate the amount of intraspecies diversity present in microbiome communities. The number of genes that were assigned to each of the seven species in each of the 1,507 metagenomic datasets were counted and compared to the number of genes found in each species' reference genome. The number of genes for a species in a community often exceeded the number found in a single isolate genome, suggesting that multiple strains of a species co-occur in vaginal bacterial communities. The total number of $L.$ $crispatus$ genes identified in each of the metagenomes where it was detected contained, on average, 1.6 times more genes (3,262±586) than were found encoded on $L.$ $crispatus$ genomes (2,064±225, P<0.001). Similar results were observed for $G.$ $vaginalis,$ $A.$ $vaginae,$ $L.$ $iners,$ $L.$ $jensenii,$ and $L.$ $gasseri.$ Among these species, $G.$ $vaginalis$ and $A.$ $vaginae$ exhibited the highest degree of intraspecies diversity, while $L.$ $crispatus$ had the highest within-metagenome intraspecies diversity among the major $Lactobacillus$ spp. These results suggest that an individual woman's vaginal bacterial population routinely comprises more than one strain of most species, and indicates that reference gene catalogs generated according to the present invention enable the investigation of this intraspecies diversity and/or leveraging of such diversity to formulate live biotherapeutics.

Well-established practices from pangenomics, e.g. the procedures described in Hervé Tettelin et al., "Genome analysis of multiple pathogenic isolates of $Streptococcus$ $agalactiae$: implications for the microbial 'pan-genome,'" 102(39) Proceedings of the National Academy of Sciences 13950 (September 2005) (the entirety of which is incorporated herein by reference), were applied to identify "core" and "accessory" non-redundant genes among the sample-specific species gene repertoires. Based on the clustering patterns of gene prevalence profiles, groups of consistently present ("core") and variably present ("accessory") non-redundant genes could be defined. The majority of the observed genes for each of the species were categorized as "accessory," with variable representation across the datasets. Using $L.$ $crispatus$ as an example, more than twice as many non-redundant genes were observed to have variable representation across the metagenomes than were present in every sample. Notably, it is clear from this analysis that the gene content identified with VIRGO in genome sequences of $L.$ $crispatus$ underrepresent the intraspecies genetic diversity present in the metagenomes. Similar results were observed for the other six species analyzed, although the magnitude of the difference between the metagenome and isolate gene repertoires varied depending on the species. Overall, VIRGO revealed that metagenomic data carry a more extensive gene content than is found in all combined isolate genome sequences.

Example 7: Metagenomic Subspecies in Vaginal Ecosystem

This Example illustrates how reference gene catalogs generated according to the present invention can be used to identify metagenomic subspecies ("MG-subspecies").

Hierarchical clustering of the metagenome species-specific gene content profiles revealed distinct groupings, defined herein as metagenomic subspecies or MG-subspecies. These metagenomic subspecies represent types of bacterial populations that share a similar gene pool as assessed by shotgun metagenomic sequence data. For example, this analysis revealed at least three distinct metagenomic subspecies for $L.$ $gasseri.$ $L.$ $gasseri$ MG-subspecies I and III have large sets of non-redundant genes that are present in one but not the others, while $L.$ $gasseri$ MG-subspecies II carries a blend of the genes from both MG-subspecies I and III. Analysis of $G.$ $vaginalis$ revealed at least five MG-subspecies, concordant with previous studies that had identified multiple clades within the species. However, it was also found that the genome-based paradigm largely underrepresents the diversity of $G.$ $vaginalis$ gene content that was identified in metagenomes. The foregoing analysis was applied to seven vaginal species, and it was found that vaginal microbial communities are often composed of complex mixtures of multiple strains of the same species, and that these mixtures can be clustered into distinct MG-subspecies. Reference gene catalogs generated according to the present invention thus enable investigation of MG-subspecies in the human microbiome and their gene contents, which in turn can reveal novel features of the microbiome and sub-populations thereof that allow for, e.g., selection, tuning, and/or optimization of strains for use in live biotherapeutic formulations.

Example 8: Gene-Specific Effect of Microbial Species on Microbiome Health

This Example illustrates the use of reference gene catalogs generated according to the present invention to formulate live biotherapeutics.

The use of VIRGO revealed a stability pattern of the microbiota from which isolates of *Lactobacillus crispatus* were cultured. Specifically, using a DBGWAS method (as described in Magali Jaillard et al., "A fast and agnostic method for bacterial genome-wide association studies: bridging the gap between k-mers and genetic events," 14(11) *PLoS Genetics* e1007758 (November 2018), the entirety of which is incorporated herein by reference) in conjunction with VIRGO, it was discovered that sequence variants of the asparagine synthase B (asnB) gene of *L. crispatus* were strongly associated with stability of *L. crispatus* in the vaginal environment, as illustrated in FIG. 8.

Metabolomics have indicated that asparagine synthase can synthesize asparagine from aspartate and glutamine (in which case glutamate is also produced) and/or from aspartate and ammonia. As has been demonstrated previously, e.g. in Pybus, two pathogenic bacteria (*G. vaginalis* and *P. bivia*) associated with bacterial vaginosis and other adverse health outcomes (e.g. inflammation, preterm birth, increased risk of STI) rely on an ammonia-based cycle to flourish in the vaginal environment. Thus, the ability of *L. crispatus* to sequester ammonia in the vagina may break this cycle and slow or prevent the growth of *G. vaginalis* and *P. bivia*. Without wishing to be bound by any particular theory, it is believed that the identified sequence variants in the asnB gene of *L. crispatus* may affect glutamine binding and thus production of asparagine by the ammonia sequestration mechanism, thereby preventing the growth of the pathogenic species and resulting in a more stable vaginal environment.

In addition to *G. vaginalis* and *P. bivia*, another common pathogen in the vaginal environment is uropathogenic *Escherichia coli* (UPEC). UPEC causes 80% of all UTI, which affects over ten million women in the United States alone each year, is highly recurrent, and is often highly antibiotic-resistant. UPEC is known to reside in the intestinal tract, but also in the vaginal tract, where it can infect the urethra and ultimately the bladder. Recurrent UTI is an unaddressed healthcare need, and live biotherapeutics that are effective against UPEC are therefore highly desirable.

Three strains of *L. crispatus* having the stability-associated asnB gene (identified herein as LUCA015, LUCA011, and LUCA09) were parallel streak assayed against UPEC, clinical *P. bivia*, and clinical *G. vaginalis* on MRS agar+1% starch. After 24 hours, the inhibiting effects of each strain against each pathogen were scored. The results of the assay are given in Table 2.

TABLE 2

|  | *E. coli* CFT073 | *P. bivia* C0046E2 | *G. vaginalis* C0047B2 |
|---|---|---|---|
| *L. crispatus* LUCA015 | +++ | +++ | +++ |
| *L. crispatus* LUCA011 | +++ | +++ | +++ |
| *L. crispatus* LUCA009 | +++ | +++ | +++ |

Legend:
− = no apparent inhibition;
+ = about 25% inhibition;
++ = about 50% inhibition;
+++ = about 75% inhibition;
++++ = apparently complete inhibition These results indicate that the effectiveness of live biotherapeutic formulations can be greatly enhanced by gene-specific selection of bacterial strains included in the live biotherapeutic formulation.

Example 9: Formulation of Gene-Specific Live Biotherapeutic

This Example further investigates the antimicrobial effect of particular *L. crispatus* strains on common vaginal pathogens.

Using the techniques described herein, nine strains of *L. crispatus* were identified as having a stability-associated asnB sequence variant, as described in the preceding Example. Aliquots of these strains were prepared according to Table 3.

TABLE 3

| ID | Strain | CFU/mL |
|---|---|---|
| 1 | LUCA111 | $7.60 \cdot 10^7$ |
| 2 | LUCA011 | $7.00 \cdot 10^8$ |
| 3 | LUCA015 | $2.16 \cdot 10^8$ |
| 4 | LUCA009 | $5.18 \cdot 10^8$ |
| 5 | LUCA102 | $3.80 \cdot 10^7$ |
| 6 | LUCA006 | $9.00 \cdot 10^7$ |
| 7 | LUCA059 | $2.18 \cdot 10^8$ |
| 8 | LUCA103 | $2.10 \cdot 10^8$ |
| 9 | LUCA008 | $1.54 \cdot 10^8$ |

Consortia, or "cocktails," comprising mixtures of four strains were also prepared according to Table 4. (In the table, "strain 1" refers to the most abundant strain in the consortium, "strain 2" to the second-most abundant strain, and so on.)

TABLE 4

| Consortium ID | Strain 1 ID | Strain 2 ID | Strain 3 ID | Strain 4 ID | CFU/mL |
|---|---|---|---|---|---|
| A | 1 | 7 | 3 | 9 | $4.74 \cdot 10^8$ |
| B | 2 | 4 | 3 | 8 | $5.20 \cdot 10^7$ |
| C | 2 | 4 | 3 | 7 | $4.50 \cdot 10^8$ |
| D | 7 | 4 | 3 | 5 | $5.72 \cdot 10^8$ |
| E | 9 | 4 | 3 | 8 | $5.40 \cdot 10^8$ |
| F | 6 | 3 | 4 | 2 | $5.48 \cdot 10^8$ |
| G | 7 | 3 | 6 | 9 | $4.08 \cdot 10^8$ |
| H | 7 | 6 | 5 | 9 | $1.10 \cdot 10^8$ |

Each of the pure strains and consortia of strains was parallel streak assayed against three vaginal pathogens on each of pure MRS agar and MRS agar+1% starch. After 24 hours, the inhibiting effects of each strain against each pathogen were scored. The results of the assay are given in Table 5.

TABLE 5

| | MRS | | | MRS + 1% starch | | |
|---|---|---|---|---|---|---|
| ID | *Prevotella* C0117C5 | UPEC CT131 | UPEC CT073 | *G. vag.* ATCC | *G. vag.* C0056B5 | UPEC CT131 |
| 1 | ++ | ++++ | ++++ | ++ | +++ | ++++ |
| 2 | ++ | ++++ | ++++ | ++ | ++++ | ++++ |
| 3 | ++ | ++++ | ++++ | ++ | +++ | ++++ |
| 4 | ++ | ++++ | ++++ | ++ | +++ | ++++ |
| 5 | + | ++++ | ++++ | + | ++ | ++++ |
| 6 | ++ | ++++ | ++++ | ++ | +++ | ++++ |
| 7 | ++ | ++++ | ++++ | — | + | +++ |
| 8 | +++ | ++++ | ++++ | +++ | ++++ | ++++ |
| 9 | ++ | ++++ | ++++ | ++ | +++ | ++++ |
| A | +++ | ++++ | ++++ | +++ | ++++ | ++++ |
| B | +++ | ++++ | ++++ | ++++ | ++++ | ++++ |
| C | +++ | ++++ | ++++ | +++ | ++++ | ++++ |
| D | ++ | ++++ | ++++ | +++ | ++++ | ++++ |
| E | ++++ | ++++ | ++++ | ++ | +++ | ++++ |
| F | ++ | ++++ | ++++ | + | ++ | ++++ |

TABLE 5-continued

| | MRS | | | MRS + 1% starch | | |
|---|---|---|---|---|---|---|
| ID | *Prevotella* C0117C5 | UPEC CT131 | UPEC CT073 | *G. vag.* ATCC | *G. vag.* C0056B5 | UPEC CT131 |
| G | ++ | ++++ | ++++ | + | +++ | ++++ |
| H | ++ | ++++ | ++++ | ++ | ND | ++++ |

Legend:
— = no apparent inhibition;
+ = about 25% inhibition;
++ = about 50% inhibition;
+++ = about 75% inhibition;
++++ = apparently complete inhibition These results indicate that the effectiveness of live biotherapeutic formulations can be greatly enhanced by gene-specific selection of bacterial strains included in the live biotherapeutic formulation, and particularly by gene-specific selection of consortia of two or more bacterial strains.

The invention illustratively disclosed herein suitably may be practiced in the absence of any element which is not specifically disclosed herein. It is apparent to those skilled in the art, however, that many changes, variations, modifications, other uses, and applications of the invention are possible, and also changes, variations, modifications, other uses, and applications which do not depart from the spirit and scope of the invention are deemed to be covered by the invention, which is limited only by the claims which follow.

The foregoing discussion of the invention has been presented for purposes of illustration and description. The foregoing is not intended to limit the invention to the form or forms disclosed herein. In the foregoing Detailed Description of the Invention, for example, various features of the invention are grouped together in one or more embodiments for the purpose of streamlining the disclosure. By way of non-limiting example, although much of the foregoing disclosure has focused on the human vaginal microbiome and features associated therewith, it is to be expressly understood that the invention is applicable, mutatis mutandis, in conjunction with other microbiomes and/or microbiotic communities, including but not limited to the human skin microbiome, the human conjunctival microbiome, the human gastrointestinal tract microbiome, the microbiome of the human urethra and bladder, the human placental microbiome, the human uterine microbiome, the human oral cavity microbiome, the human lung microbiome, the human biliary tract microbiome, and any one or more non-human microbiomes.

The features of the embodiments of the invention may be combined in alternate embodiments other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description of the Invention, with each claim standing on its own as a separate preferred embodiment of the invention.

Moreover, though the description of the invention has included description of one or more embodiments and certain variations and modifications, other variations, combinations, and modifications are within the scope of the invention, e.g. as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

The invention claimed is:

1. A method for achieving an improvement in the vaginal health of a female human subject, comprising:
   administering a remedial live biotherapeutic formulation to the subject,
   wherein the remedial live biotherapeutic formulation comprises bacteria adapted to remedy wherein the remedial live biotherapeutic formulation comprises bacteria adapted to remedy a deficiency or excess of at least one bacterial strain in the subject's vaginal microbial community,
   wherein the bacteria comprise a selected strain or consortium of strains comprising at least one of:
   (i) *Lactobacillus crispatus* bacteria configured to express at least one of the asparagine synthase B (asnB) gene of SEQ ID NO: 2 and the asparagine synthase B (asnB) gene of SEQ ID NO: 3; and
   (ii) *Lactobacillus crispatus* bacteria containing an asparagine synthase B (asnb) gene encoding at least one of a polypeptide of SEQ ID NO: 5 and a polypeptide of SEQ ID NO: 6, and
   wherein the improvement is selected from the group consisting of decreasing ammonia in the vaginal environment of the subject, reducing inflammation in the subject, suppressing the growth or hampering the survival of at least one of *Gardnerella vaginalis* and *Prevotella bivia* in the vagina of the subject, and combinations thereof.

2. The method of claim 1, wherein the selected strain or consortium of strains comprises at least one strain selected from the group consisting of LUCA111, LUCA011, LUCA015, LUCA009, LUCA102, LUCA006, LUCA059, LUCA103, and LUCA008.

3. The method of claim 1, wherein the live biotherapeutic formulation further comprises a pharmaceutically acceptable carrier.

4. The method of claim 1, wherein the live biotherapeutic formulation further comprises an agent adapted to reduce or remove free ammonia from the vaginal environment.

5. The method of claim 1, wherein the *Lactobacillus crispatus* bacteria are configured to express the asparagine synthase B (asnB) gene of SEQ ID NO: 2.

6. The method of claim 1, wherein the *Lactobacillus crispatus* bacteria are configured to express the asparagine synthase B (asnB) gene of SEQ ID NO: 3.

7. The method of claim 1, wherein the *Lactobacillus crispatus* bacteria containing an asparagine synthase B (asnB) gene encode the polypeptide of SEQ ID NO: 5.

8. The method of claim 1, wherein the *Lactobacillus crispatus* bacteria containing an asparagine synthase B (asnB) gene encode the polypeptide of SEQ ID NO: 6.

9. The method of claim 1, wherein the live biotherapeutic formulation further comprises a redox potential control agent.

10. The method of claim 1, wherein the live biotherapeutic formulation further comprises a pH buffer configured to maintain a healthy pH of the vaginal environment.

11. The method of claim 1, wherein the live biotherapeutic formulation further comprises an antimicrobial agent.

12. The method of claim 1, wherein the live biotherapeutic formulation further comprises a growth promoter.

13. A method for achieving an improvement in the vaginal health of a female human subject, comprising:
    administering a remedial live biotherapeutic formulation to the subject,
    wherein the remedial live biotherapeutic formulation comprises bacteria adapted to remedy a deficiency or excess of at least one bacterial strain in the subject's vaginal microbial community,
    wherein the bacteria comprise a selected strain or consortium of strains comprising at least one of:
    (i) *Lactobacillus crispatus* bacteria configured to express at least one of the asparagine synthase B (asnB) gene of SEQ ID NO: 2 and the asparagine synthase B (asnB) gene of SEQ ID NO: 3; and
    (ii) *Lactobacillus crispatus* bacteria containing an asparagine synthase B (asnB) gene encoding at least one of a polypeptide of SEQ ID NO: 5 and a polypeptide of SEQ ID NO: 6, and wherein the improvement comprises decreasing ammonia in the vaginal environment of the subject.

14. The method of claim 13, wherein the live biotherapeutic formulation further comprises at least one of an antimicrobial agent, a redox potential control agent and a pH buffer configured to maintain a healthy pH of the vaginal environment.

15. The method of claim 13, wherein the live biotherapeutic formulation further comprises a redox potential control agent.

16. The method of claim 13, wherein the live biotherapeutic formulation further comprises a pH buffer configured to maintain a healthy pH of the vaginal environment.

17. A method for achieving an improvement in the vaginal health of a female human subject, comprising:

administering a remedial live biotherapeutic formulation to the subject, wherein the remedial live biotherapeutic formulation comprises bacteria adapted to remedy a deficiency or excess of at least one bacterial strain in the subject's vaginal microbial community, wherein the bacteria comprise a selected strain or consortium of strains comprising at least one of:

(i) *Lactobacillus crispatus* bacteria configured to express at least one of the asparagine synthase B (asnB) gene of SEQ ID NO: 2 and the asparagine synthase B (asnB) gene of SEQ ID NO: 3; and (ii) *Lactobacillus crispatus* bacteria containing an asparagine synthase B (asnB) gene encoding at least one of a polypeptide of SEQ ID NO: 5 and a polypeptide of SEQ ID NO: 6, and wherein the improvement comprises reducing inflammation in the subject.

18. The method of claim 17, wherein the live biotherapeutic formulation further comprises at least one of an antimicrobial agent, a redox potential control agent and a pH buffer configured to maintain a healthy pH of the vaginal environment.

19. The method of claim 17, wherein the live biotherapeutic formulation further comprises an antimicrobial agent.

20. The method of claim 17, wherein the method further comprises suppressing the growth or hampering the survival of at least one of *Gardnerella vaginalis* and *Prevotella bivia* in the vagina of the subject.

* * * * *

UNITED STATES PATENT AND TRADEMARK OFFICE
CERTIFICATE OF CORRECTION

| | |
|---|---|
| PATENT NO. | : 11,389,491 B2 |
| APPLICATION NO. | : 17/223710 |
| DATED | : July 19, 2022 |
| INVENTOR(S) | : Jacques Ravel et al. |

It is certified that error appears in the above-identified patent and that said Letters Patent is hereby corrected as shown below:

In the Claims

In Claim 1, Column 45, Lines 34-39 please delete "wherein the remedial live biotherapeutic formulation comprises bacteria adapted to remedy wherein the remedial live biotherapeutic formulation comprises bacteria adapted to remedy a deficiency or excess of at least one bacterial strain in the subject's vaginal microbial community," and insert
-- wherein the remedial live biotherapeutic formulation comprises bacteria adapted to remedy a deficiency or excess of at least one bacterial strain in the subject's vaginal microbial community, --

Signed and Sealed this
Third Day of January, 2023

*Katherine Kelly Vidal*

Katherine Kelly Vidal
*Director of the United States Patent and Trademark Office*

SEQUENCE LISTING

<160> NUMBER OF SEQ ID NOS: 6

<210> SEQ ID NO 1
<211> LENGTH: 1950
<212> TYPE: DNA
<213> ORGANISM: Lactobacillus crispatus

<400> SEQUENCE: 1

```
atgtgcggaa ttgtcgcatt ttatgatcca aaaataaacg aaaaacaagc cgttattggt      60
aagatgatgg ctactatcaa gcaccgtgga cctaattccg acggttatta cactaatgat     120
gaggttgccc ttggtttcag aagattgtca attatcgatc ttcgtggggg agctcaacct     180
atttataatg aagataaaac tagagcaatt atctttaatg gtgaaattta caactttaaa     240
ccattaagag aacaattaat taaagcaggc cacactttca ctaccaaggc cgatactgaa     300
gtattgcttc acggttatga agagtggggc atggatggcc ttcttaagaa ggtacgtggt     360
atgtttgcct tccttatttg ggatgacaac aacaagaccc tttatggtgc acgtgacttc     420
tttggtatta agccaatgta ctacagcaac caagatggcc acttacttgt aggttcagaa     480
cttaagagtt tcttggaata tccaaagttc aagcgtgaat tgaacgttga agctgttaag     540
ccatacctca tgaaccaata caacgacctt gaagaaacct tctttaaagg cgtttacaga     600
ttcccagcag gtcactggtt cgaatacaaa gatggtgaaa tgaagaccca ccaatactgg     660
gatgcggaat acaaggaaaa tagtttaagc tttgaagaaa ctttgaagcg tatcaacgat     720
```

-continued

```
gacttgaagg aaaccgttga tttgtacaga attgctgacg ttaaggttgg tgcattcttg      780
tcagaaggta ttgactcttc atacttgact actttgctta acccagacga tgttttctca      840
gtaagttttg atgactcaac ttacgatgaa gcttcaaagg ctaaggcatt agctgacatc      900
aaccactgga agttctacag tgacaaggtt gatgccgacg aagctatgcg tgattttcca      960
gaaatgcaat accacatgga tgaaccagat gccaacccat caatcatccc actttggtac     1020
ttgtgtaagt tagctcgtaa gcacgttact gttgcacttt ctggtgaagg tgccgacgaa     1080
ttatttgctg gctacgttaa ctacgggatg catacgcata acgacattat aaggtctttt     1140
acttcagaat tgaaaaagtt gcctgagaag aagcgggtta aattggcaca caagattaag     1200
agaatgccta atttcccagg taaagttcac atgtacacca atttagctga accgagtgaa     1260
ttttatgtcg gtcaatcggt tatctatgac atggattacc caactatctt tacttctaaa     1320
gatgctaata gcattttaca gccaacgtat cgcaataaat tgactgttaa cggcatttac     1380
caaaaagact ttaagaaagt aaagggagtc gataatgtta agcagatgca atacattgac     1440
ttgcaccact ttatgcttaa cgatattgaa caaaaagctg ataagatttc gatggcccat     1500
tcacttgaag ttcgtgttcc ttacctcgac aagaagattg cggaattggc taactctatc     1560
ccaaccaagt acttggttaa ccgtcatgat accaagtatg ctttgcgtaa ggcttcagaa     1620
aaagttttac agatgagtg ggctaagaga cctaagcttg cttcccaac tccaattaag      1680 caatggttga ggaaccacg ttttttacaaa caagttcatg ctcttttga agaagaattt       1740 gtcaacgata ttttttgacca aaagaagatt atcaagttac ttgacgacaa ctatgaaggt     1800
gatggctcac atagacgtca aatctgggct atctacacct tccttgtttg gtacaagttg     1860
ttctttgttg attacgaaaa cacagttaag aaatatcaac acgtgcaacc tgaagttgct     1920
aagctaattt cacagggcaa attactataa                                       1950
```

<210> SEQ ID NO 2
<211> LENGTH: 1950
<212> TYPE: DNA
<213> ORGANISM: Lactobacillus crispatus

<400> SEQUENCE: 2

```
atgtgcggaa ttgtcgcgtt ttatgatcca agataaatg aaaagcaggc tgtcattggc        60
aaaatgatgg ccacgattaa acaccgcgga cctagttccg acgggtatta tactaatgac      120
gaggttgccc ttggttttag aagattatca attattgatc ttcgtggggg tagccaacct      180
atttataatg aagataaaac tagagcaatt attttttaatg gtgaaattta aactttttaag    240 ccattaagag aagaattaat taaagcaggc catgatttta ctactaaggc tgatacagaa      300
gtcttacttc atggttatga agaatggggc atggatggct tgcttaagcg tgtacgtggg      360
atgttcgcct tcttaatttg ggatgacaac aacaagaccc tttatggtgc acgtgacttc      420
tttggcatta agccaatgta ctacagtaat caaaatggcc atttgttggt tggttcagaa      480
ttaaagagct ttttggaatt tccaaagttc aagcgggaat taaatgttga agcagttaag      540
ccatacttga tgaatcaata caatgaccta gaagaaacct tctttaaggg cgtttaccgc      600
ttcccagcgg gccattggtt tgaatacaaa gatggtgaaa tgaagaccca tcaatattgg      660
gatgctgaat ataaagaaaa tagccttttcc tttgaagaaa ctttgcaaaa gatcaacgaa      720
gatttgaaag aaacggttga tttgtataga aacgctgatg ttaaggttgg tgcttttctta     780 tcagaaggaa tcgactcttc atacttgact agtttgctta acccagatga cgttttctca      840
gtaagttttg atgattcaac ttatgatgaa gcttctaagg ctaaggcatt agcagatatt      900
```

-continued

```
aatcactgga agttcttcag cgataaggtt gatgctgatg aagcaatgcg tgacttccca      960
gaaatgcaat accacatgga tgaaccagat gctaatccgt caatcattcc actctggtac     1020
ttgtgtaaac tagctcgtaa gcatgttact gttgctcttt caggtgaagg cgctgatgaa     1080
ttgtttgctg gttatgtgaa ctacgggatg catacgcata acgacattat taaggtcttt     1140
acttcagaat tgaaaaagtt gcctgagaag aagcgggtta aattggcaca caagattaag     1200
agaatgccta atttcccagg taaagttcac atgtacacca atttagctga accgagtgaa     1260
ttttatgtcg gtcaatcggt tatctatgac atggattacc caactatctt tacttctaaa     1320
gatgctaata gcattttaca gccaacgtat cgcaataaat tgactgttaa cggcatttac     1380
caaaaagact ttaagaaagt aaagggagtc gataatgtta agcagatgca atacattgac     1440
ttgcaccact ttatgcttaa cgatattgaa caaaaagctg ataagatttc gatggcccat     1500
tcacttgaag ttcgtgttcc ttacctcgac aagaagattg cggaattggc taactctatc     1560
ccaaccaagt acttggttaa ccgtcatgat accaagtatg ctttgcgtaa ggcttcagaa     1620
aaagttttac agatgagtg gctaagaga cctaagcttg gcttcccaac tccaattaag      1680
caatggttga aggaaccacg tttttacaaa caagttcatg ctcttttga agaagaattt      1740 gtcaacgata ttttgacca aaagaagatt atcaagttac ttgacgacaa ctatgaaggt      1800
gatggctcac atagacgtca aatctgggct atctatacct tccttgtttg gtacaagttg     1860
ttctttgttg attacgaaaa cacagttaag aaatatcaac acgtgcaacc tgaagttgct     1920
aagctaattt cacagggtaa attactataa                                      1950

<210> SEQ ID NO 3
<211> LENGTH: 1948
<212> TYPE: DNA
<213> ORGANISM: Lactobacillus crispatus

<400> SEQUENCE: 3
atgtgcggaa ttgtcgcgtt ttatgatcca aagataaatg aaaagcaggc tgtcattggc       60
aaaatgatgg ccacgattaa acaccgcgga cctagttccg acgggtatta tactaatgac      120
gaggttgccc ttggttttag aagattatca attattgatc ttcgtggggg tagccaacct      180
atttataatg aagataaaac tagagcaatt attttttaatg gtgaaattta taacttttaag     240 ccattaagag aagaattaat taagcaggc catgatttta ctactaaggc tgatacagaa       300
gtcttacttc atggttatga agaatgggc atggatggct tgcttaagcg tgtacgtggg      360
atgttcgcct tcttaatttg ggatgacaac aacaagaccc tttatggtgc acgtgacttc      420
tttggcatta agccaatgta ctacagtaat caaaatggcc atttgttggt tggttcagaa      480
ttaaagagct ttttggaatt tccaaagttc aagcgggaat taaatgttga agcagttaag      540
ccatacttga tgaatcaata caatgaccta aagaaacct tctttaaggg catttaccgc       600
ttcccagcgg gccattggtt tgaatacaaa gatggtgaaa tgaagaccca tcaatattgg      660
gatgctgaat ataaagaaaa tagccttttcc tttgaagaaa ctttgcaaaa gatcaacgaa      720
gatttgaaag aaacggttga tttgtataga aacgctgatg ttaaggttgg tgctttctta      780
tcagaaggaa tcgactcttc atacttgact agttttgctta acccagatga cgttttctca     840
gtaagttttg atgattcaac ttatgatgaa gcttctaagg ctaaggcatt agcagatatt       900
aatcctggaa gttcttcagc gatmggttga tgctgatgaa gcaatgcgtg acttcccaga     960
aatgcaatac cacatggatg aaccagatgc taatccgtca atcattccac tctggtactt     1020
gtgtaaacta gctcgtaagc atgttactgt tgctctttca ggtgaaggcg ctgatgaatt     1080
```

```
gtttgctggt tatgtgaact acgggatgca tacgcataac gacattatta aggtctttac    1140
ttcagaattg aaaaagttgc ctgagaagaa gcgggttaaa ttggcacaca agattaagag    1200
aatgcctaat ttcccaggta aagttcacat gtacaccaat ttagctgaac cgagtgaatt    1260
ttatgtcggt caatcggtta tctatgacat ggattaccca actatcttta cttctaaaga    1320
tgctaatagc attttacagc caacgtatcg caataaattg actgttaacg gcatttacca    1380
aaaagacttt aagaaagtaa agggagtcga taatgttaag cagatgcaat acattgactt    1440
gcaccacttt atgcttaacg atattgaaca aaaagctgat aagatttcga tggcccattc    1500
acttgaagtt cgtgttcctt acctcgacaa gaagattgcg gaattggcta actctatccc    1560
aaccaagtac ttggttaacc gtcatgatac caagtatgct ttgcgtaagg cttcagaaaa    1620
agttttacca gatgagtggg ctaagagacc taagcttggc ttcccaactc caattaagca    1680
atggttgaag gaaccacgtt tttacaaaca agttcatgcc ttttttgaag aagaatttgt    1740
caacgatatt tttgaccaaa agaagattat caagttactt gacgacaact atgaaggtga    1800
tggctcacat agacgtcaaa tctgggctat ctataccttc cttgtttggt acaagttgtt    1860
ctttgttgat tacgaaaaca cagttaagaa atatcaacac gtgcaacctg aagttgctaa    1920
gctaatttca cagggtaaat tactataa                                       1948
```

<210> SEQ ID NO 4
<211> LENGTH: 650
<212> TYPE: PRT
<213> ORGANISM: Lactobacillus crispatus

<400> SEQUENCE: 4

Met Cys Gly Ile Val Ala Phe Tyr Asp Pro Lys Ile Asn Glu Lys Gln
1               5                   10                  15

Ala Val Ile Gly Lys Met Met Ala Thr Ile Lys His Arg Gly Pro Asn
            20                  25                  30

Ser Asp Gly Tyr Tyr Thr Asn Asp Glu Val Ala Leu Gly Phe Arg Arg
        35                  40                  45

Leu Ser Ile Ile Asp Leu Arg Gly Gly Ala Gln Pro Ile Tyr Asn Glu
    50                  55                  60

Asp Lys Thr Arg Ala Ile Ile Phe Asn Gly Glu Ile Tyr Asn Phe Lys
65                  70                  75                  80

Pro Leu Arg Glu Gln Leu Ile Lys Ala Gly His Thr Phe Thr Thr Lys
                85                  90                  95

Ala Asp Thr Glu Val Leu Leu His Gly Tyr Glu Glu Trp Gly Met Asp
            100                 105                 110

Gly Leu Leu Lys Lys Val Arg Gly Met Phe Ala Phe Leu Ile Trp Asp
        115                 120                 125

Asp Asn Asn Lys Thr Leu Tyr Gly Ala Arg Asp Phe Phe Gly Ile Lys
    130                 135                 140

Pro Met Tyr Tyr Ser Asn Gln Asp Gly His Leu Leu Val Gly Ser Glu
145                 150                 155                 160

Leu Lys Ser Phe Leu Glu Tyr Pro Lys Phe Lys Arg Glu Leu Asn Val
                165                 170                 175

Glu Ala Val Lys Pro Tyr Leu Met Asn Gln Tyr Asn Asp Leu Glu Glu
            180                 185                 190

Thr Phe Phe Lys Gly Trp Arg Phe Pro Ala Gly His Trp Phe Glu Tyr
        195                 200                 205

Lys Asp Gly Glu Met Lys Thr His Gln Tyr Trp Asp Ala Glu Tyr Lys
    210                 215                 220

-continued

Glu Asn Ser Leu Ser Phe Glu Glu Thr Leu Lys Arg Ile Asn Asp Asp
225                 230                 235                 240

Leu Lys Glu Thr Val Asp Leu Tyr Arg Ile Ala Asp Val Lys Val Gly
            245                 250                 255

Ala Phe Leu Ser Glu Gly Ile Asp Ser Ser Tyr Leu Thr Thr Leu Leu
            260                 265                 270

Asn Pro Asp Asp Val Phe Ser Val Ser Phe Asp Ser Thr Tyr Asp
        275                 280                 285

Glu Ala Ser Lys Ala Lys Ala Leu Ala Asp Ile Asn His Leu Ala Leu
        290                 295                 300

Lys Phe Tyr Ser Asp Lys Val Asp Ala Asp Glu Ala Met Arg Asp Phe
305                 310                 315                 320

Pro Glu Met Gln Tyr His Met Asp Glu Pro Asp Ala Asn Pro Ser Ile
            325                 330                 335

Ile Pro Leu Trp Tyr Leu Cys Lys Leu Ala Arg Lys His Val Thr Val
            340                 345                 350

Ala Leu Ser Gly Glu Gly Ala Asp Glu Leu Phe Ala Gly Tyr Val Asn
            355                 360                 365

Tyr Gly Met His Thr His Asn Asp Ile Ile Lys Val Phe Thr Ser Glu
            370                 375                 380

Leu Lys Lys Leu Pro Glu Lys Lys Arg Val Lys Leu Ala His Lys Ile
385                 390                 395                 400

Lys Arg Met Pro Asn Phe Pro Gly Lys Val His Met Tyr Thr Asn Leu
                405                 410                 415

Ala Glu Pro Ser Glu Phe Tyr Val Gly Gln Ser Val Ile Tyr Asp Met
            420                 425                 430

Asp Tyr Pro Thr Ile Phe Thr Ser Lys Asp Ala Asn Ser Ile Leu Gln
            435                 440                 445

Pro Thr Tyr Arg Asn Lys Leu Thr Val Asn Gly Ile Tyr Gln Lys Asp
            450                 455                 460

Phe Lys Lys Val Lys Gly Val Asp Asn Val Lys Gln Met Gln Tyr Ile
465                 470                 475                 480

Asp Leu His His Phe Met Leu Asn Asp Ile Glu Gln Lys Ala Asp Lys
                485                 490                 495

Ile Ser Met Ala His Ser Leu Glu Val Arg Val Pro Tyr Leu Asp Lys
            500                 505                 510

Lys Ile Ala Glu Leu Ala Asn Ser Ile Pro Thr Lys Tyr Leu Val Asn
            515                 520                 525

Arg His Asp Thr Lys Tyr Ala Leu Arg Lys Ala Ser Glu Lys Val Leu
530                 535                 540

Pro Asp Glu Trp Ala Lys Arg Pro Lys Leu Gly Phe Pro Thr Pro Ile
545                 550                 555                 560

Lys Gln Trp Leu Lys Glu Pro Arg Phe Tyr Lys Gln Val His Ala Leu
            565                 570                 575

Phe Glu Glu Glu Phe Val Asn Asp Ile Phe Asp Gln Lys Lys Ile Ile
            580                 585                 590

Lys Leu Leu Asp Asp Asn Tyr Glu Gly Asp Gly Ser His Arg Arg Gln
            595                 600                 605

Ile Trp Ala Ile Tyr Thr Phe Leu Val Trp Tyr Lys Leu Phe Phe Val
610                 615                 620

```
Asp Tyr Glu Asn Thr Val Lys Lys Tyr Gln His Val Gln Pro Glu Val
625                 630                 635                 640

Ala Lys Leu Ile Ser Gln Gly Lys Leu Leu
            645                 650

<210> SEQ ID NO 5
<211> LENGTH: 651
<212> TYPE: PRT
<213> ORGANISM: Lactobacillus crispatus

<400> SEQUENCE: 5

Met Cys Gly Ile Val Ala Phe Tyr Asp Pro Lys Ile Asn Glu Lys Gln
1               5                   10                  15

Ala Val Ile Gly Lys Met Met Ala Thr Ile Lys His Arg Gly Pro Ser
            20                  25                  30

Ser Asp Gly Tyr Tyr Thr Asn Asp Glu Val Ala Leu Gly Phe Arg Arg
        35                  40                  45

Leu Ser Ile Ile Asp Leu Arg Gly Gly Ser Gln Pro Ile Tyr Asn Glu
    50                  55                  60

Asp Lys Thr Arg Ala Ile Ile Phe Asn Gly Glu Ile Tyr Asn Phe Lys
65                  70                  75                  80

Pro Leu Arg Glu Glu Leu Ile Lys Ala Gly His Asp Phe Thr Thr Lys
                85                  90                  95

Ala Asp Thr Glu Val Leu Leu His Gly Tyr Glu Glu Trp Gly Met Asp
            100                 105                 110

Gly Leu Leu Lys Arg Val Arg Gly Met Phe Ala Phe Leu Ile Trp Asp
        115                 120                 125

Asp Asn Asn Lys Thr Leu Tyr Gly Ala Arg Asp Phe Phe Gly Ile Lys
130                 135                 140

Pro Met Tyr Tyr Ser Asn Gln Asn Gly His Leu Leu Val Gly Ser Glu
145                 150                 155                 160

Leu Lys Ser Phe Leu Glu Phe Pro Lys Phe Lys Arg Glu Leu Asn Val
                165                 170                 175

Glu Ala Val Lys Pro Tyr Leu Met Asn Gln Tyr Asn Asp Leu Glu Glu
            180                 185                 190

Thr Phe Phe Lys Gly Val Tyr Arg Phe Pro Ala Gly His Trp Phe Glu
        195                 200                 205

Tyr Lys Asp Gly Glu Met Lys Thr His Gln Tyr Leu Ala Leu Asp Ala
210                 215                 220

Glu Tyr Lys Glu Asn Ser Leu Ser Phe Glu Glu Thr Leu Gln Lys Ile
225                 230                 235                 240

Asn Glu Asp Leu Lys Glu Thr Val Asp Leu Tyr Arg Asn Ala Asp Val
                245                 250                 255

Lys Val Gly Ala Phe Leu Ser Glu Gly Ile Asp Ser Ser Tyr Leu Thr
            260                 265                 270

Ser Leu Leu Asn Pro Asp Asp Val Phe Ser Val Ser Phe Asp Asp Ser
        275                 280                 285

Thr Tyr Asp Glu Ala Ser Lys Ala Lys Ala Leu Ala Asp Ile Asn His
290                 295                 300

Trp Lys Phe Phe Ser Asp Lys Val Asp Ala Asp Glu Ala Met Arg Asp
305                 310                 315                 320

Phe Pro Glu Met Gln Tyr His Met Asp Glu Pro Asp Ala Asn Pro Ser
                325                 330                 335

Ile Ile Pro Leu Trp Tyr Leu Cys Lys Leu Ala Arg Lys His Val Thr
            340                 345                 350
```

```
Val Ala Leu Ser Gly Glu Gly Ala Asp Glu Leu Phe Ala Gly Tyr Val
            355                 360                 365

Asn Tyr Gly Met His Thr His Asn Asp Ile Ile Lys Val Phe Thr Ser
370                 375                 380

Glu Leu Lys Lys Leu Pro Glu Lys Lys Arg Val Lys Leu Ala His Lys
385                 390                 395                 400

Ile Lys Arg Met Pro Asn Phe Pro Gly Lys Val His Met Tyr Thr Asn
                405                 410                 415

Leu Ala Glu Pro Ser Glu Phe Tyr Val Gly Gln Ser Val Ile Tyr Asp
                420                 425                 430

Met Asp Tyr Pro Thr Ile Phe Thr Ser Lys Asp Ala Asn Ser Ile Leu
            435                 440                 445

Gln Pro Thr Tyr Arg Asn Lys Leu Thr Val Asn Gly Ile Tyr Gln Lys
450                 455                 460

Asp Phe Lys Lys Val Lys Gly Val Asp Asn Val Lys Gln Met Gln Tyr
465                 470                 475                 480

Ile Asp Leu His His Phe Met Leu Asn Asp Ile Glu Gln Lys Ala Asp
                485                 490                 495

Lys Ile Ser Met Ala His Ser Leu Glu Val Arg Val Pro Tyr Leu Asp
                500                 505                 510

Lys Lys Ile Ala Glu Leu Ala Asn Ser Ile Pro Thr Lys Tyr Leu Val
            515                 520                 525

Asn Arg His Asp Thr Lys Tyr Ala Leu Arg Lys Ala Ser Glu Lys Val
530                 535                 540

Leu Pro Asp Glu Trp Ala Lys Arg Pro Lys Leu Gly Phe Pro Thr Pro
545                 550                 555                 560

Ile Lys Gln Trp Leu Lys Glu Pro Arg Phe Tyr Lys Gln Val His Ala
                565                 570                 575

Leu Phe Glu Glu Glu Phe Val Asn Asp Ile Phe Asp Gln Lys Lys Ile
                580                 585                 590

Ile Lys Leu Leu Asp Asp Asn Tyr Glu Gly Asp Gly Ser His Arg Arg
            595                 600                 605

Gln Ile Trp Ala Ile Tyr Thr Phe Leu Val Trp Tyr Lys Leu Phe Phe
610                 615                 620

Val Asp Tyr Glu Asn Thr Val Lys Lys Tyr Gln His Val Gln Pro Glu
625                 630                 635                 640

Val Ala Lys Leu Ile Ser Gln Gly Lys Leu Leu
                645                 650

<210> SEQ ID NO 6
<211> LENGTH: 651
<212> TYPE: PRT
<213> ORGANISM: Lactobacillus crispatus

<400> SEQUENCE: 6

Met Cys Gly Ile Val Ala Phe Tyr Asp Pro Lys Ile Asn Glu Lys Gln
1               5                   10                  15

Ala Val Ile Gly Lys Met Met Ala Thr Ile Lys His Arg Gly Pro Ser
            20                  25                  30

Ser Asp Gly Tyr Tyr Thr Asn Asp Glu Val Ala Leu Gly Phe Arg Arg
        35                  40                  45

Leu Ser Ile Ile Asp Leu Arg Gly Gly Ser Gln Pro Ile Tyr Asn Glu
50                  55                  60

Asp Lys Thr Arg Ala Ile Ile Phe Asn Gly Glu Ile Tyr Asn Phe Lys
65                  70                  75                  80
```

-continued

```
Pro Leu Arg Glu Glu Leu Ile Lys Ala Gly His Asp Phe Thr Thr Lys
                 85                  90                  95
Ala Asp Thr Glu Val Leu Leu His Gly Tyr Glu Glu Trp Gly Met Asp
            100                 105                 110
Gly Leu Leu Lys Arg Val Arg Gly Met Phe Ala Phe Leu Ile Trp Asp
        115                 120                 125
Asp Asn Asn Lys Thr Leu Tyr Gly Ala Arg Asp Phe Phe Gly Ile Lys
    130                 135                 140
Pro Met Tyr Tyr Ser Asn Gln Asn Gly His Leu Leu Val Gly Ser Glu
145                 150                 155                 160
Leu Lys Ser Phe Leu Glu Phe Pro Lys Phe Lys Arg Glu Leu Asn Val
                165                 170                 175
Glu Ala Val Lys Pro Tyr Leu Met Asn Gln Tyr Asn Asp Leu Glu Glu
            180                 185                 190
Thr Phe Phe Lys Gly Ile Tyr Arg Phe Pro Ala Gly His Trp Phe Glu
        195                 200                 205
Tyr Lys Asp Gly Glu Met Lys Thr His Gln Tyr Trp Asp Ala Glu Tyr
    210                 215                 220
Lys Glu Asn Ser Leu Ser Phe Glu Glu Thr Leu Gln Lys Ile Asn Glu
225                 230                 235                 240
Asp Leu Lys Glu Thr Val Asp Leu Tyr Arg Asn Ala Asp Val Lys Val
                245                 250                 255
Gly Ala Phe Leu Ser Glu Gly Ile Asp Ser Ser Tyr Leu Thr Ser Leu
            260                 265                 270
Leu Asn Pro Asp Asp Val Phe Ser Val Ser Phe Asp Asp Ser Thr Tyr
        275                 280                 285
Asp Glu Ala Ser Lys Ala Lys Ala Leu Ala Asp Ile Asn His Trp Lys
    290                 295                 300
Phe Phe Ser Asp Lys Val Asp Ala Asp Glu Ala Met Arg Asp Phe Pro
305                 310                 315                 320
Glu Met Gln Tyr His Met Asp Glu Pro Asp Ala Asn Pro Ser Ile Ile
                325                 330                 335
Pro Leu Trp Tyr Leu Cys Lys Leu Ala Arg Lys His Val Thr Val Ala
            340                 345                 350
Leu Ser Gly Glu Gly Ala Asp Glu Leu Phe Ala Gly Tyr Val Asn Tyr
        355                 360                 365
Gly Met His Thr His Asn Asp Ile Ile Lys Val Phe Thr Ser Glu Leu
    370                 375                 380
Lys Lys Leu Pro Glu Lys Lys Arg Val Lys Leu Ala His Lys Ile Lys
385                 390                 395                 400
Arg Met Pro Asn Phe Pro Gly Lys Val His Met Tyr Thr Asn Leu Ala
                405                 410                 415
Glu Pro Ser Glu Phe Tyr Val Gly Gln Ser Val Ile Tyr Asp Met Asp
            420                 425                 430
Tyr Pro Thr Ile Phe Thr Ser Lys Asp Ala Asn Ser Ile Leu Gln Pro
        435                 440                 445
Thr Tyr Arg Asn Lys Leu Thr Val Asn Gly Ile Tyr Gln Lys Asp Phe
    450                 455                 460
Lys Lys Val Lys Gly Val Asp Asn Val Lys Gln Met Gln Tyr Ile Asp
465                 470                 475                 480
Leu His His Phe Met Leu Asn Asp Ile Glu Gln Lys Ala Asp Lys Ile
                485                 490                 495
```

```
Ser Met Ala His Ser Leu Glu Val Arg Val Pro Tyr Leu Asp Lys Lys
            500             505             510

Ile Ala Glu Leu Ala Asn Ser Ile Pro Thr Lys Tyr Leu Val Asn Arg
        515             520             525

His Asp Thr Lys Tyr Ala Leu Arg Lys Ala Ser Glu Lys Val Leu Pro
    530             535             540

Asp Glu Trp Ala Lys Arg Pro Lys Leu Gly Phe Pro Thr Pro Ile Lys
545             550             555             560

Gln Trp Leu Lys Glu Pro Arg Phe Tyr Lys Gln Val His Ala Leu Phe
                565             570             575

Glu Glu Glu Phe Val Asn Asp Ile Phe Asp Gln Lys Lys Ile Ile Lys
            580             585             590

Leu Leu Asp Asp Asn Tyr Glu Gly Asp Gly Ser His Arg Arg Gln Ile
        595             600             605

Trp Ala Ile Tyr Thr Phe Leu Val Leu Ala Leu Tyr Lys Leu Phe Phe
    610             615             620

Val Asp Tyr Glu Asn Thr Val Lys Lys Tyr Gln His Val Gln Pro Glu
625             630             635             640

Val Ala Lys Leu Ile Ser Gln Gly Lys Leu Leu
            645             650
```